US011845779B2

(12) United States Patent
Dal Peraro et al.

(10) Patent No.: US 11,845,779 B2
(45) Date of Patent: Dec. 19, 2023

(54) MUTANT AEROLYSIN AND USES THEREOF

(71) Applicant: ECOLE POLYTECHNIQUE FEDERALE DE LAUSANNE (EPFL), Lausanne (CH)

(72) Inventors: Matteo Dal Peraro, Préverenges (CH); Chan Cao, Ecublens (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 275 days.

(21) Appl. No.: 17/082,682

(22) Filed: Oct. 28, 2020

(65) Prior Publication Data
US 2022/0127310 A1  Apr. 28, 2022

(51) Int. Cl.
C07K 14/195 (2006.01)
G01N 27/447 (2006.01)
G01N 33/487 (2006.01)

(52) U.S. Cl.
CPC ..... *C07K 14/195* (2013.01); *G01N 27/44791* (2013.01); *G01N 33/48721* (2013.01)

(58) Field of Classification Search
None
See application file for complete search history.

(56) References Cited

U.S. PATENT DOCUMENTS

2009/0016988 A1* 1/2009 Buckley ................ A61P 35/00
536/23.7
2013/0045192 A1* 2/2013 Movalia ............. A61K 38/4886
514/56

FOREIGN PATENT DOCUMENTS

WO    WO 2003/018611 A2 *  3/2003

OTHER PUBLICATIONS

Y.-Q. Wang, et al., "Rationally Designed Sensing Selectivity and Sensitivity of an Aerolysin Nanopore via Site-Directed Mutagenesis", ACS Sensors, 3(4): p. 779-783, April (Year: 2018).*
J. Wang, et al., "Direct Quantification of Damaged Nucleotide in Oligonucleotides Using an Aerolysin Single Molecule Interface", ACS Central Science, 6(1): p. 76-82; January (Year: 2020).*
Y. Lu, et al., "Simultaneous single-molecule discrimination of cysteine and homocysteine with a protein nanopore", Chemical Communication, 55(63): p. 9311-9314 (Year: 2019).*
Jiajun Wang et al, "Direct Quantification of Damaged Nucleotides in Oligonucleotides Using an Aerolysin Single Molecule Interface," ACS Central Science, 2020, vol. 6, pp. 76-82.

(Continued)

*Primary Examiner* — J. Christopher Ball
(74) *Attorney, Agent, or Firm* — Oliff PLC

(57) ABSTRACT

Aerolysin polypeptides and/or mutant aerolysin monomers include modified amino acid sequences that could have improved substrate analyte, such as (poly)nucleotide and peptide, improved reading properties such as enhanced substrate analyte capture and improved substrate analyte recognition and/or discrimination. Also, aerolysin pores may be derived from the mutant monomers as well as apparatuses and devices may include modified aerolysin polypeptides. Further, methods of using modified aerolysin proteins and pores derive therefrom may be used in characterizing and/or sequencing a polymeric molecule or may be for use as molecular sensors.

13 Claims, 6 Drawing Sheets
Specification includes a Sequence Listing.

(56) References Cited

OTHER PUBLICATIONS

Xue-yuan Wu et al, "Design and Construction of an Aerolysin Single-Molecule Interface for Single-Molecule Sensing," Biophysical Journal, 2020, vol. 118, Issue 3, Supplement 1, 481A (1 page).
Shuang Li et al, "T232K/K238Q Aerolysin Nanopore for Mapping Adjacent Phosphorylation Sites of a Single Tau Peptide," Small Methods, 2020, 2000014 (6 pages).
Si-Min Lu et al, "Diversified Exploitation of Aerolysin Nanopore in Single-Molecule Sensing and Protein Sequencing," VIEW, 2020, 20200006 (6 pages).
Chan Cao et al, "Single-Molecule Sensing of Peptides and Nucleic Acids by Engineered Aerolysin Nanopores," Nature Communications, Oct. 29, 2019, vol. 10, Article No. 4918 (11 pages).
Chan Cao, Single-molecule sensing of peptides and nucleic acids by engineered aerolysin nanopores, 26 pages, Oct. 29, 2019, http://www.nature.com/naturecommunications, https://doi.org/10/1038/s41467-019-12690-9, Nature Communications, (2019) 10:4918.†
Si-Min Lu, Diversified exploitation of aerolysin nanopore in single-molecule sensing and protein sequencing, 6 pages, Aug. 9, 2022, https://onlinelibrary.wiley.com/ , https://doi.org/10.1002/VIW.20200006 , VIEW. (2020) 1:20200006.†
Chan Cao, Mapping the sensing spots of aerolysin for single oligonucleotides analysis, 9 pages, Jul. 19, 2018, http://www.nature.com/naturecommunications, https://doi.org/10.1038/s41467-018-05108-5, Nature Communications , (2018) 9:2823.†

\* cited by examiner
† cited by third party

SEQUENCE LISTING

<160> NUMBER OF SEQ ID NOS: 15

<210> SEQ ID NO 1
<211> LENGTH: 470
<212> TYPE: PRT
<213> ORGANISM: Aeromonas hydrophila

<400> SEQUENCE: 1

Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
            35                  40                  45

Gly Leu Ala Asn Gly Trp Val Ile Met Gly Pro Gly Tyr Asn Gly Glu
50                      55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
            115                 120                 125

Gly Gly Asn His Ser Gln Tyr Val Gly Glu Asp Met Asp Val Thr Arg
130                     135                 140

Asp Gly Asp Gly Trp Val Ile Arg Gly Asn Asn Asp Gly Gly Cys Asp
145                     150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Gly Trp Ala Val Asn Asp Ser
            195                 200                 205

Asp Thr Pro Gln Ser Gly Tyr Asp Val Thr Leu Arg Tyr Asp Thr Ala
            210                 215                 220

Thr Asn Trp Ser Lys Thr Asn Thr Tyr Gly Leu Ser Glu Lys Val Thr
225                     230                 235                 240

Thr Lys Asn Lys Phe Lys Trp Pro Leu Val Gly Glu Thr Glu Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
            275                 280                 285

Ser Lys Ile Pro Val Lys Ile Glu Leu Tyr Lys Ala Asp Ile Ser Tyr
            290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
                340                 345                 350

Ser Ser Ile Arg Tyr Gln Trp Asp Lys Arg Tyr Ile Pro Gly Glu Val
            355                 360                 365

Lys Trp Trp Asp Trp Asn Trp Thr Ile Gln Gln Asn Gly Leu Ser Thr
            370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Ser Lys Val Arg Arg Ala Arg
            420                 425                 430

-continued

Ser Val Asp Gly Ala Gly Gln Gly Leu Arg Leu Glu Ile Pro Leu Asp
            435                 440                 445

Ala Gln Glu Leu Ser Gly Leu Gly Phe Asn Asn Val Ser Leu Ser Val
    450                 455                 460

Thr Pro Ala Ala Asn Gln
465             470

<210> SEQ ID NO 2
<211> LENGTH: 462
<212> TYPE: PRT
<213> ORGANISM: Aeromonas hydrophila

<400> SEQUENCE: 2

Ala Glu Pro Val Tyr Pro Asp Gln Leu Arg Leu Phe Ser Leu Gly Gln
1               5                   10                  15

Glu Val Cys Gly Asp Lys Tyr Arg Pro Ile Thr Arg Glu Glu Ala Gln
            20                  25                  30

Ser Val Lys Ser Asn Ile Val Asn Met Met Gly Gln Trp Gln Ile Ser
        35                  40                  45

Gly Leu Ala Asn Gly Trp Val Ile Met Gly Pro Val Tyr Asn Gly Glu
    50                  55                  60

Ile Lys Pro Gly Ser Ala Ser Asn Thr Trp Cys Tyr Pro Val Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Glu
145                 150                 155                 160

Gly Tyr Arg Cys Gly Glu Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Ile Asn Asp Ser
        195                 200                 205

Tyr Thr Pro Gln Ser Ala Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Glu Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285

Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

```
Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
        355                 360                 365

Lys Trp Trp Asp Trp Asn Trp Thr Ile Gln Gln Asn Gly Leu Ser Thr
370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
            405                 410                 415

Gly Ala Pro Val Pro Leu Ala Ala Asp Gly Lys Ala Pro Arg Ala Leu
        420                 425                 430

Ser Ala Arg Arg Gly Glu Gln Gly Leu Arg Leu Ala Ile Pro Leu Glu
        435                 440                 445

Cys Arg Lys Ser Ser Pro Gly Leu Ala Ser Ala Thr Ser Ala
    450                 455                 460

<210> SEQ ID NO 3
<211> LENGTH: 464
<212> TYPE: PRT
<213> ORGANISM: Aeromonas sobria

<400> SEQUENCE: 3

Ala Glu Pro Val Tyr Pro Asp Gln Val Lys Trp Ala Gly Leu Gly Thr
1               5                   10                  15

Gly Val Cys Ala Ser Gly Tyr Arg Pro Leu Thr Arg Asp Glu Ala Met
            20                  25                  30

Ser Ile Lys Gly Asn Leu Val Ser Arg Met Gly Gln Trp Gln Ile Thr
        35                  40                  45

Gly Leu Ala Asp Arg Trp Val Ile Met Gly Pro Gly Tyr Asn Gly Glu
    50                  55                  60

Ile Lys Gln Gly Thr Ala Gly Glu Thr Trp Cys Tyr Pro Asn Ser Pro
65                  70                  75                  80

Val Ser Gly Glu Ile Pro Thr Leu Ser Asp Trp Asn Ile Pro Ala Gly
                85                  90                  95

Asp Glu Val Asp Val Gln Trp Arg Leu Val His Asp Asn Asp Tyr Phe
            100                 105                 110

Ile Lys Pro Val Ser Tyr Leu Ala His Tyr Leu Gly Tyr Ala Trp Val
        115                 120                 125

Gly Gly Asn His Ser Pro Tyr Val Gly Glu Asp Met Asp Val Thr Arg
    130                 135                 140

Val Gly Asp Gly Trp Leu Ile Lys Gly Asn Asn Asp Gly Gly Cys Ser
145                 150                 155                 160

Gly Tyr Arg Cys Gly Glu Lys Ser Ser Ile Lys Val Ser Asn Phe Ser
                165                 170                 175

Tyr Thr Leu Glu Pro Asp Ser Phe Ser His Gln Val Thr Glu Ser
            180                 185                 190

Gly Lys Gln Leu Val Lys Thr Ile Thr Ala Asn Ala Thr Asn Tyr Thr
        195                 200                 205

Asp Leu Pro Gln Gln Val Val Thr Leu Lys Tyr Asp Lys Ala Thr
    210                 215                 220

Asn Trp Ser Lys Thr Asp Thr Tyr Ser Leu Ser Glu Lys Val Thr Thr
225                 230                 235                 240

Lys Asn Lys Phe Gln Trp Pro Leu Val Gly Glu Thr Glu Leu Ala Ile
```

```
            245                 250                 255
Glu Ile Ala Ala Ser Gln Ser Trp Ala Ser Gln Lys Gly Gly Ser Thr
            260                 265                 270

Thr Glu Thr Val Ser Val Glu Ala Arg Pro Thr Val Pro Pro His Ser
        275                 280                 285

Ser Leu Pro Val Arg Val Ala Leu Tyr Lys Ser Asn Ile Ser Tyr Pro
        290                 295                 300

Tyr Glu Phe Lys Ala Glu Val Asn Tyr Asp Leu Thr Met Lys Gly Phe
305                 310                 315                 320

Leu Arg Trp Gly Gly Asn Ala Trp Tyr Thr His Pro Asp Asn Arg Pro
                325                 330                 335

Thr Trp Glu His Thr Leu Leu Leu Gly Pro Phe Arg Gly Gln Gly Glu
            340                 345                 350

Gln His Pro Leu Pro Val Asp Lys Arg Tyr Ile Pro Gly Glu Val Lys
            355                 360                 365

Trp Trp Asp Trp Asn Trp Thr Ile Ser Glu Tyr Gly Leu Ser Thr Met
370                 375                 380

Gln Asn Asn Leu Gly Arg Val Leu Arg Pro Ile Arg Ser Ala Val Thr
385                 390                 395                 400

Gly Asp Phe Tyr Ala Glu Ser Gln Phe Ala Gly Asp Ile Glu Ile Gly
                405                 410                 415

Gln Pro Gln Thr Arg Ser Ala Lys Ala Ala Gln Leu Arg Ser Ala Ser
            420                 425                 430

Ala Glu Glu Val Ala Leu Thr Ser Val Asp Leu Asp Ser Glu Ala Leu
            435                 440                 445

Ala Asn Glu Gly Phe Gly Asn Val Ser Leu Thr Ile Val Pro Val Gln
            450                 455                 460

<210> SEQ ID NO 4
<211> LENGTH: 469
<212> TYPE: PRT
<213> ORGANISM: Aeromonas hydrophila

<400> SEQUENCE: 4

Ala Glu Pro Val Tyr Pro Asp Gln Leu Arg Leu Phe Ser Leu Gly Gln
1               5                   10                  15

Glu Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Ser Ala Ser Ser Thr Trp Cys Tyr Pro Thr Asn Pro
65                  70                  75                  80

Ala Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160
```

```
Gly Tyr Arg Cys Gly Asp Lys Thr Ser Ile Lys Val Ser Asn Phe Ala
            165                 170                 175

Tyr Asn Leu Asp Pro Asp Ser Phe Lys His Gly Asp Val Thr Gln Ser
        180                 185                 190

Asp Arg Gln Leu Val Lys Thr Val Gly Trp Ala Ile Asn Asp Ser
        195                 200                 205

Asp Thr Pro Gln Ser Gly Tyr Asp Val Thr Leu Arg Tyr Asp Thr Ala
        210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Glu Leu Ser
                245                 250                 255

Ile Glu Ile Ala Ala Asn Gln Ser Trp Ala Ser Gln Asn Gly Gly Ser
            260                 265                 270

Pro Thr Thr Ser Leu Ser Gln Ser Val Arg Pro Thr Val Pro Ala His
        275                 280                 285

Ser Lys Ile Pro Val Lys Ile Glu Leu Tyr Lys Ala Asp Ile Ser Tyr
        290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
        355                 360                 365

Lys Trp Trp Asp Trp Asn Trp Thr Ile Gln Gln Asn Gly Leu Pro Thr
370                 375                 380

Met Gln Asn Asn Leu Ala Lys Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Val Ala Ala Ala Ser His Ser Ser Arg Ala Arg
            420                 425                 430

Asn Leu Ser Ala Gly Gln Gly Leu Arg Leu Glu Ile Pro Leu Asp Ala
        435                 440                 445

Gln Glu Leu Ser Gly Leu Gly Phe Asn Asn Val Ser Leu Ser Val Thr
        450                 455                 460

Pro Ala Ala Asn Gln
465

<210> SEQ ID NO 5
<211> LENGTH: 471
<212> TYPE: PRT
<213> ORGANISM: Aeromonas enteropelogenes

<400> SEQUENCE: 5

Asn Ala Ala Glu Pro Ile Tyr Pro Asp Gln Leu Arg Leu Phe Ser Leu
1               5                   10                  15

Gly Glu Asp Val Cys Gly Thr Asp Tyr Arg Pro Ile Asn Arg Glu Glu
            20                  25                  30

Ala Gln Ser Val Arg Asn Asn Ile Val Ala Met Met Gly Gln Trp Gln
        35                  40                  45

Ile Ser Gly Leu Ala Asn Asn Trp Val Ile Leu Gly Pro Gly Tyr Asn
    50                  55                  60
```

```
Gly Glu Ile Lys Pro Gly Lys Ala Ser Thr Thr Trp Cys Tyr Pro Thr
 65                  70                  75                  80

Arg Pro Ala Thr Ala Glu Ile Pro Val Leu Pro Ala Phe Asn Ile Pro
                 85                  90                  95

Asp Gly Asp Ala Val Asp Val Gln Trp Arg Met Val His Asp Ser Ala
            100                 105                 110

Asn Phe Ile Lys Pro Val Ser Tyr Leu Ala His Tyr Leu Gly Tyr Ala
        115                 120                 125

Trp Val Gly Gly Asp His Ser Gln Phe Val Gly Asp Met Asp Val
130                 135                 140

Ile Gln Glu Gly Asp Trp Val Leu Arg Gly Asn Asp Gly Gly Lys
145                 150                 155                 160

Cys Asp Gly Tyr Arg Cys Asn Glu Lys Ser Ser Ile Arg Val Ser Asn
                165                 170                 175

Phe Ala Tyr Thr Leu Asp Pro Gly Ser Phe Ser His Gly Asp Val Thr
            180                 185                 190

Gln Ser Glu Arg Thr Leu Val His Thr Val Gly Trp Ala Thr Asn
        195                 200                 205

Ile Ser Asp Thr Pro Gln Ser Gly Tyr Asp Val Thr Leu Asn Tyr Thr
210                 215                 220

Thr Met Ser Asn Trp Ser Lys Thr Asn Thr Tyr Gly Leu Ser Glu Lys
225                 230                 235                 240

Val Ser Thr Lys Asn Lys Phe Lys Trp Pro Leu Val Gly Glu Thr Glu
                245                 250                 255

Val Ser Ile Glu Ile Ala Ala Asn Gln Ser Trp Ala Ser Gln Asn Gly
            260                 265                 270

Gly Ala Val Thr Thr Ala Leu Ser Gln Ser Val Arg Pro Val Val Pro
        275                 280                 285

Ala Arg Ser Arg Val Pro Val Lys Ile Glu Leu Tyr Lys Ala Asn Ile
290                 295                 300

Ser Tyr Pro Tyr Glu Phe Lys Ala Asp Met Ser Tyr Asp Leu Thr Phe
305                 310                 315                 320

Asn Gly Phe Leu Arg Trp Gly Gly Asn Ala Trp His Thr His Pro Glu
                325                 330                 335

Asp Arg Pro Thr Leu Ser His Thr Phe Ala Ile Gly Pro Phe Lys Asp
            340                 345                 350

Lys Ala Ser Ser Ile Arg Tyr Gln Trp Asp Lys Arg Tyr Leu Pro Gly
        355                 360                 365

Glu Met Lys Trp Trp Asp Trp Asn Trp Ala Ile Gln Gln Asn Gly Leu
370                 375                 380

Ala Thr Met Gln Asp Ser Leu Ala Arg Val Leu Arg Pro Val Arg Ala
385                 390                 395                 400

Ser Ile Thr Gly Asp Phe Arg Ala Glu Ser Gln Phe Ala Gly Asn Ile
                405                 410                 415

Glu Ile Gly Thr Pro Val Pro Leu Gly Ser Asp Ser Lys Val Arg Arg
            420                 425                 430

Thr Arg Ser Val Asp Gly Ala Asn Thr Gly Leu Lys Leu Asp Ile Pro
        435                 440                 445

Leu Asp Ala Gln Glu Leu Ala Glu Leu Gly Phe Glu Asn Val Thr Leu
450                 455                 460

Ser Val Thr Pro Ala Arg Asn
465                 470
```

<210> SEQ ID NO 6
<211> LENGTH: 465
<212> TYPE: PRT
<213> ORGANISM: Aeromonas salmonicida

<400> SEQUENCE: 6

```
Trp His Glu Pro Val Tyr Pro Asp Gln Val Lys Trp Ala Gly Leu Gly
1               5                  10                  15

Thr Gly Val Cys Ala Ser Gly Tyr Arg Pro Leu Thr Arg Asp Glu Ala
                20                  25                  30

Met Ser Ile Lys Gly Asn Leu Val Ser Arg Met Gly Gln Trp Gln Ile
            35                  40                  45

Thr Gly Leu Ala Asp Arg Trp Val Ile Met Gly Pro Gly Tyr Asn Gly
        50                  55                  60

Glu Ile Lys Gln Gly Thr Ala Gly Glu Thr Trp Cys Tyr Pro Asn Ser
65                  70                  75                  80

Pro Val Ser Gly Glu Ile Pro Thr Leu Ser Asp Trp Asn Ile Pro Ala
                85                  90                  95

Gly Asp Glu Val Asp Val Gln Trp Arg Leu Val His Asp Asn Asp Tyr
            100                 105                 110

Phe Ile Lys Pro Val Ser Tyr Leu Ala His Tyr Leu Gly Tyr Ala Trp
        115                 120                 125

Val Gly Gly Asn His Ser Pro Tyr Val Gly Glu Asp Met Asp Val Thr
    130                 135                 140

Arg Val Gly Asp Gly Trp Leu Ile Lys Gly Asn Asn Asp Gly Gly Cys
145                 150                 155                 160

Ser Gly Tyr Arg Cys Gly Glu Lys Ser Ser Ile Lys Val Ser Asn Phe
                165                 170                 175

Ser Tyr Thr Leu Glu Pro Asp Ser Phe Ser His Gly Gln Val Thr Glu
            180                 185                 190

Ser Gly Lys Gln Leu Val Lys Thr Ile Thr Ala Asn Ala Thr Asn Tyr
        195                 200                 205

Thr Asp Leu Pro Gln Gln Val Val Thr Leu Lys Tyr Asp Lys Ala
    210                 215                 220

Thr Asn Trp Ser Lys Thr Asp Thr Tyr Ser Leu Ser Glu Lys Val Thr
225                 230                 235                 240

Thr Lys Asn Lys Phe Gln Trp Pro Leu Val Gly Glu Thr Glu Leu Ala
                245                 250                 255

Ile Glu Ile Ala Ala Ser Gln Ser Trp Ala Ser Gln Lys Gly Gly Ser
            260                 265                 270

Thr Thr Glu Thr Val Ser Val Glu Ala Arg Pro Thr Val Pro Pro His
        275                 280                 285

Ser Ser Leu Pro Val Arg Val Ala Leu Tyr Lys Ser Asn Ile Ser Tyr
    290                 295                 300

Pro Tyr Glu Phe Lys Ala Glu Val Asn Tyr Asp Leu Thr Met Lys Gly
305                 310                 315                 320

Phe Leu Arg Trp Gly Gly Asn Ala Trp Tyr Thr His Pro Asp Asn Arg
                325                 330                 335

Pro Thr Trp Glu His Thr Phe Arg Leu Gly Pro Phe Arg Gly Gln Gly
            340                 345                 350

Glu Gln His Pro Leu Pro Val Asp Lys Arg Tyr Ile Pro Gly Glu Val
        355                 360                 365

Lys Trp Trp Asp Trp Asn Trp Thr Ile Ser Glu Tyr Gly Leu Ser Thr
    370                 375                 380
```

```
Met Gln Asn Asn Leu Gly Arg Val Leu Arg Pro Ile Arg Ser Ala Val
385                 390                 395                 400

Thr Gly Asp Phe Tyr Ala Glu Ser Gln Phe Ala Gly Asp Ile Glu Ile
            405                 410                 415

Gly Gln Pro Gln Thr Arg Ser Ala Lys Ala Ala Gln Leu Arg Ser Ala
        420                 425                 430

Ser Ala Glu Glu Val Ala Leu Thr Ser Val Asp Leu Asp Ser Glu Ala
        435                 440                 445

Leu Ala Asn Glu Gly Phe Gly Asn Val Ser Leu Thr Ile Val Pro Val
    450                 455                 460

Gln
465

<210> SEQ ID NO 7
<211> LENGTH: 469
<212> TYPE: PRT
<213> ORGANISM: Aeromonas hydrophila

<400> SEQUENCE: 7

Ala Glu Pro Val Tyr Pro Asp Gln Leu Arg Leu Phe Ser Leu Gly Gln
1               5                   10                  15

Glu Val Cys Gly Asp Lys Tyr Arg Pro Val Asn Arg Glu Glu Ala Gln
            20                  25                  30

Ser Ile Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Ser Ala Ser Ser Thr Trp Cys Tyr Pro Thr Asn Pro
65                  70                  75                  80

Ala Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ser Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Gly Trp Ala Ile Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Glu Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala His
```

```
                275                 280                 285
Ser Lys Ile Pro Val Lys Ile Glu Leu Tyr Lys Ala Asp Ile Ser Tyr
290                 295                 300

Pro Tyr Glu Phe Lys Ala Asp Val Ser Tyr Asp Leu Thr Leu Ser Gly
305                 310                 315                 320

Phe Leu Arg Trp Gly Asn Ala Trp Tyr Thr His Pro Asp Asn Arg
                325                 330                 335

Pro Asn Trp Asn His Thr Phe Val Ile Gly Pro Tyr Lys Asp Lys Ala
                340                 345                 350

Ser Ser Ile Arg Tyr Gln Trp Asp Lys Arg Tyr Ile Pro Gly Glu Val
                355                 360                 365

Lys Trp Trp Asp Trp Asn Trp Thr Ile Gln Gln Asn Gly Leu Pro Thr
370                 375                 380

Met Gln Asn Asn Leu Ala Lys Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Val Ala Ala Ser His Ser Ser Arg Ala Arg
                420                 425                 430

Asn Leu Ser Ala Gly Gln Gly Leu Arg Leu Glu Ile Pro Leu Asp Ala
                435                 440                 445

Gln Glu Leu Ser Gly Leu Gly Phe Asn Asn Val Ser Leu Ser Val Thr
450                 455                 460

Pro Ala Ala Asn Gln
465

<210> SEQ ID NO 8
<211> LENGTH: 422
<212> TYPE: PRT
<213> ORGANISM: Aeromonas hydrophila

<400> SEQUENCE: 8

Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
                20                  25                  30

Ser Val Lys Ser Asn Ile Val Gly Met Met Gly Gln Trp Gln Ile Ser
                35                  40                  45

Gly Leu Ala Asn Gly Trp Val Ile Met Gly Pro Gly Tyr Asn Gly Glu
50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
                100                 105                 110

Ile Lys Pro Thr Ser Tyr Leu Ala His Tyr Leu Gly Tyr Ala Trp Val
                115                 120                 125

Gly Gly Asn His Ser Gln Tyr Val Gly Glu Asp Met Asp Val Thr Arg
                130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175
```

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Glu Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285

Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
        355                 360                 365

Lys Trp Trp Asp Trp Asn Trp Thr Ile Gln Asn Gly Leu Ser Thr
    370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu
            420

<210> SEQ ID NO 9
<211> LENGTH: 1392
<212> TYPE: DNA
<213> ORGANISM: Aeromonas hydrophila

<400> SEQUENCE: 9
gcagagcccg tctatccaga ccagcttcgc ttgttttcat tgggccaagg ggtctgtggc     60
gacaagtatc gccccgtcaa tcgagaagaa gcccaaagcg ttaaaagcaa tattgtcggc    120
atgatggggc aatggcaaat aagcgggctg gccaacggct gggtcattat ggggccgggt    180
tataacggtg aaataaaacc agggacagcg tccaatacct ggtgttatcc gaccaatcct    240
gttaccggtg aaataccgac actgtctgcc ctggatattc agatggtga cgaagtcgat    300
gtgcagtggc gactggtaca tgacagtgcg aatttcatca accaaccag ctatctggcc    360
cattacctcg gttatgcctg ggtgggcggc aatcacagcc aatatgtcgg cgaagacatg    420
gatgtgaccc gtgatggcga cggctgggtg atccgtggca acaatgacgg cggctgtgac    480
ggctatcgct gtggtgacaa gacggccatc aaggtcagca acttcgccta aacctggat    540
cccgacagct tcaagcatgg cgatgtcacc cagtccgacc gccagctggt caagactgtg    600
gtgggctggg cggtcaacga cagcgacacc cccaatccg gctatgacgt caccctgcgc    660
tacgacacag ccaccaactg gtccaagacc aacacctatg gcctgagcga aaggtgacc    720

```
accaagaaca agttcaagtg gccactggtg ggggaaaccc aactctccat cgagattcgt   780
gccaatcagt cctgggcgtc ccagaacggg ggctcgacca ccacctccct gtctcagtcc   840
gtgcgaccga ctgtgccggc ccgctccaag atcccggtga agatagagct ctacaaggcc   900
gacatctcct atccctatga gttcaaggcc gatgtcagct atgacctgac cctgagcggc   960
ttcctgcgct ggggcggcaa cgcctggtat acccacccgg acaaccgtcc gaactggaac  1020
cacaccttcg tcataggtcc gtacaaggac aaggcgagca gcattcgcta ccagtgggac  1080
aagcgttaca tcccgggtga agtgaagtgg tgggactgga actggaccat acagcagaac  1140
ggtctgtcta ccatgcagaa caacctggcc agagtgctgc cccggtgcg gcgggggatc  1200
accggtgatt tcagtgccga gccagttt gccggcaaca tagagatcgg tgctcccgtg  1260
ccgctcgcgg ctgacagcaa ggtgcgtcgt gctcgcagtg tggacggcgc tggtcaaggc  1320
ctgaggctgg agatcccgct cgatcgcgaa gagctctccg gcttggctt caacaagtca  1380
gcctcagcgt ga                                                      1392
```

<210> SEQ ID NO 10
<211> LENGTH: 422
<212> TYPE: PRT
<213> ORGANISM: Aeromonas hydrophila

<400> SEQUENCE: 10

```
Ala Glu Pro Val Tyr Pro Asp Gln Leu Arg Leu Phe Ser Leu Gly Gln
1               5                   10                  15

Glu Val Cys Gly Asp Lys Tyr Arg Pro Ile Thr Arg Glu Glu Ala Gln
            20                  25                  30

Ser Val Lys Ser Asn Ile Val Asn Met Met Gly Gln Trp Gln Ile Ser
        35                  40                  45

Gly Leu Ala Asn Gly Trp Val Ile Met Gly Pro Val Tyr Asn Gly Glu
    50                  55                  60

Ile Lys Pro Gly Ser Ala Ser Asn Thr Trp Cys Tyr Pro Val Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Glu
145                 150                 155                 160

Gly Tyr Arg Cys Gly Glu Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Gly Trp Ala Ile Asn Asp Ser
        195                 200                 205

Tyr Thr Pro Gln Ser Ala Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Glu Leu Ser
```

-continued

```
                245                 250                 255
Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
            275                 280                 285

Ser Lys Ile Pro Val Lys Ile Glu Leu Tyr Lys Ala Asp Ile Ser Tyr
            290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
                340                 345                 350

Ser Ser Ile Arg Tyr Gln Trp Asp Lys Arg Tyr Ile Pro Gly Glu Val
                355                 360                 365

Lys Trp Trp Asp Trp Asn Trp Thr Ile Gln Gln Asn Gly Leu Ser Thr
370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu
            420
```

<210> SEQ ID NO 11
<211> LENGTH: 419
<212> TYPE: PRT
<213> ORGANISM: Aeromonas sobria

<400> SEQUENCE: 11

```
Ala Glu Pro Val Tyr Pro Asp Gln Val Lys Trp Ala Gly Leu Gly Thr
1               5                   10                  15

Gly Val Cys Ala Ser Gly Tyr Arg Pro Leu Thr Arg Asp Glu Ala Met
                20                  25                  30

Ser Ile Lys Gly Asn Leu Val Ser Arg Met Gly Gln Trp Gln Ile Thr
            35                  40                  45

Gly Leu Ala Asp Arg Trp Val Ile Met Gly Pro Gly Tyr Asn Gly Glu
        50                  55                  60

Ile Lys Gln Gly Thr Ala Gly Glu Thr Trp Cys Tyr Pro Asn Ser Pro
65                  70                  75                  80

Val Ser Gly Glu Ile Pro Thr Leu Ser Asp Trp Asn Ile Pro Ala Gly
                85                  90                  95

Asp Glu Val Asp Val Gln Trp Arg Leu Val His Asp Asn Asp Tyr Phe
            100                 105                 110

Ile Lys Pro Val Ser Tyr Leu Ala His Tyr Leu Gly Tyr Ala Trp Val
        115                 120                 125

Gly Gly Asn His Ser Pro Tyr Val Gly Glu Asp Met Asp Val Thr Arg
    130                 135                 140

Val Gly Asp Gly Trp Leu Ile Lys Gly Asn Asn Asp Gly Gly Cys Ser
145                 150                 155                 160

Gly Tyr Arg Cys Gly Glu Lys Ser Ser Ile Lys Val Ser Asn Phe Ser
                165                 170                 175

Tyr Thr Leu Glu Pro Asp Ser Phe Ser His Gly Gln Val Thr Glu Ser
            180                 185                 190
```

Gly Lys Gln Leu Val Lys Thr Ile Thr Ala Asn Ala Thr Asn Tyr Thr
            195                 200                 205

Asp Leu Pro Gln Gln Val Val Thr Leu Lys Tyr Asp Lys Ala Thr
210                 215                 220

Asn Trp Ser Lys Thr Asp Thr Tyr Ser Leu Ser Glu Lys Val Thr Thr
225                 230                 235                 240

Lys Asn Lys Phe Gln Trp Pro Leu Val Gly Thr Glu Leu Ala Ile
            245                 250                 255

Glu Ile Ala Ala Ser Gln Ser Trp Ala Ser Gln Lys Gly Gly Ser Thr
                260                 265                 270

Thr Glu Thr Val Ser Val Glu Ala Arg Pro Thr Val Pro Pro His Ser
            275                 280                 285

Ser Leu Pro Val Arg Val Ala Leu Tyr Lys Ser Asn Ile Ser Tyr Pro
290                 295                 300

Tyr Glu Phe Lys Ala Glu Val Asn Tyr Asp Leu Thr Met Lys Gly Phe
305                 310                 315                 320

Leu Arg Trp Gly Gly Asn Ala Trp Tyr Thr His Pro Asp Asn Arg Pro
                325                 330                 335

Thr Trp Glu His Thr Leu Leu Leu Gly Pro Phe Arg Gly Gln Gly Glu
            340                 345                 350

Gln His Pro Leu Pro Val Asp Lys Arg Tyr Ile Pro Gly Glu Val Lys
            355                 360                 365

Trp Trp Asp Trp Asn Trp Thr Ile Ser Glu Tyr Gly Leu Ser Thr Met
370                 375                 380

Gln Asn Asn Leu Gly Arg Val Leu Arg Pro Ile Arg Ser Ala Val Thr
385                 390                 395                 400

Gly Asp Phe Tyr Ala Glu Ser Gln Phe Ala Gly Asp Ile Glu Ile Gly
                405                 410                 415

Gln Pro Gln

<210> SEQ ID NO 12
<211> LENGTH: 422
<212> TYPE: PRT
<213> ORGANISM: Aeromonas hydrophila

<400> SEQUENCE: 12

Ala Glu Pro Val Tyr Pro Asp Gln Leu Arg Leu Phe Ser Leu Gly Gln
1               5                   10                  15

Glu Val Cys Gly Asp Lys Tyr Arg Pro Val Asn Arg Glu Glu Ala Gln
                20                  25                  30

Ser Val Lys Ser Asn Ile Val Gly Met Met Gly Gln Trp Gln Ile Ser
            35                  40                  45

Gly Leu Ala Asn Gly Trp Val Ile Met Gly Pro Gly Tyr Asn Gly Glu
        50                  55                  60

Ile Lys Pro Gly Ser Ala Ser Ser Thr Trp Cys Tyr Pro Thr Asn Pro
65                  70                  75                  80

Ala Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

```
Asp Gly Asp Gly Trp Val Ile Arg Gly Asn Asn Asp Gly Gly Cys Asp
145                 150                 155                 160

Gly Tyr Arg Cys Gly Asp Lys Thr Ser Ile Lys Val Ser Asn Phe Ala
            165                 170                 175

Tyr Asn Leu Asp Pro Asp Ser Phe Lys His Gly Asp Val Thr Gln Ser
        180                 185                 190

Asp Arg Gln Leu Val Lys Thr Val Gly Trp Ala Ile Asn Asp Ser
    195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Glu Leu Ser
            245                 250                 255

Ile Glu Ile Ala Ala Asn Gln Ser Trp Ala Ser Gln Asn Gly Gly Ser
            260                 265                 270

Pro Thr Thr Ser Leu Ser Gln Ser Val Arg Pro Thr Val Pro Ala His
            275                 280                 285

Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
            325                 330                 335

Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
            355                 360                 365

Lys Trp Trp Asp Trp Asn Trp Thr Ile Gln Gln Asn Gly Leu Pro Thr
            370                 375                 380

Met Gln Asn Asn Leu Ala Lys Val Leu Arg Pro Val Arg Ala Gly Ile
385                 390                 395                 400

Thr Gly Asp Phe Ser Ala Glu Ser Gln Phe Ala Gly Asn Ile Glu Ile
            405                 410                 415

Gly Ala Pro Val Pro Val
            420

<210> SEQ ID NO 13
<211> LENGTH: 424
<212> TYPE: PRT
<213> ORGANISM: Aeromonas enteropelogenes

<400> SEQUENCE: 13

Asn Ala Ala Glu Pro Ile Tyr Pro Asp Gln Leu Arg Leu Phe Ser Leu
1               5                   10                  15

Gly Glu Asp Val Cys Gly Thr Asp Tyr Arg Pro Ile Asn Arg Glu Glu
            20                  25                  30

Ala Gln Ser Val Arg Asn Asn Ile Val Ala Met Met Gly Gln Trp Gln
        35                  40                  45

Ile Ser Gly Leu Ala Asn Asn Trp Val Ile Leu Gly Pro Gly Tyr Asn
    50                  55                  60

Gly Glu Ile Lys Pro Gly Lys Ala Ser Thr Thr Trp Cys Tyr Pro Thr
65                  70                  75                  80

Arg Pro Ala Thr Ala Glu Ile Pro Val Leu Pro Ala Phe Asn Ile Pro
            85                  90                  95
```

```
Asp Gly Asp Ala Val Asp Val Gln Trp Arg Met Val His Asp Ser Ala
            100                 105                 110

Asn Phe Ile Lys Pro Val Ser Tyr Leu Ala His Tyr Leu Gly Tyr Ala
            115                 120                 125

Trp Val Gly Gly Asp His Ser Gln Phe Val Gly Asp Asp Met Asp Val
130                 135                 140

Ile Gln Glu Gly Asp Asp Trp Val Leu Arg Gly Asn Asp Gly Gly Lys
145                 150                 155                 160

Cys Asp Gly Tyr Arg Cys Asn Glu Lys Ser Ser Ile Arg Val Ser Asn
                165                 170                 175

Phe Ala Tyr Thr Leu Asp Pro Gly Ser Phe Ser His Gly Asp Val Thr
            180                 185                 190

Gln Ser Glu Arg Thr Leu Val His Thr Val Val Gly Trp Ala Thr Asn
            195                 200                 205

Ile Ser Asp Thr Pro Gln Ser Gly Tyr Asp Val Thr Leu Asn Tyr Thr
            210                 215                 220

Thr Met Ser Asn Trp Ser Lys Thr Asn Thr Tyr Gly Leu Ser Glu Lys
225                 230                 235                 240

Val Ser Thr Lys Asn Lys Phe Lys Trp Pro Leu Val Gly Glu Thr Glu
                245                 250                 255

Val Ser Ile Glu Ile Ala Ala Asn Gln Ser Trp Ala Ser Gln Asn Gly
            260                 265                 270

Gly Ala Val Thr Thr Ala Leu Ser Gln Ser Val Arg Pro Val Val Pro
            275                 280                 285

Ala Arg Ser Arg Val Pro Val Lys Ile Glu Leu Tyr Lys Ala Asn Ile
            290                 295                 300

Ser Tyr Pro Tyr Glu Phe Lys Ala Asp Met Ser Tyr Asp Leu Thr Phe
305                 310                 315                 320

Asn Gly Phe Leu Arg Trp Gly Gly Asn Ala Trp His Thr His Pro Glu
                325                 330                 335

Asp Arg Pro Thr Leu Ser His Thr Phe Ala Ile Gly Pro Phe Lys Asp
            340                 345                 350

Lys Ala Ser Ser Ile Arg Tyr Gln Trp Asp Lys Arg Tyr Leu Pro Gly
            355                 360                 365

Glu Met Lys Trp Trp Asp Trp Asn Trp Ala Ile Gln Gln Asn Gly Leu
370                 375                 380

Ala Thr Met Gln Asp Ser Leu Ala Arg Val Leu Arg Pro Val Arg Ala
385                 390                 395                 400

Ser Ile Thr Gly Asp Phe Arg Ala Glu Ser Gln Phe Ala Gly Asn Ile
                405                 410                 415

Glu Ile Gly Thr Pro Val Pro Leu
            420

<210> SEQ ID NO 14
<211> LENGTH: 420
<212> TYPE: PRT
<213> ORGANISM: Aeromonas salmonicida

<400> SEQUENCE: 14

Trp His Glu Pro Val Tyr Pro Asp Gln Val Lys Trp Ala Gly Leu Gly
1               5                   10                  15

Thr Gly Val Cys Ala Ser Gly Tyr Arg Pro Leu Thr Arg Asp Glu Ala
            20                  25                  30

Met Ser Ile Lys Gly Asn Leu Val Ser Arg Met Gly Gln Trp Gln Ile
```

```
            35                  40                  45
Thr Gly Leu Ala Asp Arg Trp Val Ile Met Gly Pro Gly Tyr Asn Gly
 50                  55                  60

Glu Ile Lys Gln Gly Thr Ala Gly Glu Thr Trp Cys Tyr Pro Asn Ser
 65                  70                  75                  80

Pro Val Ser Gly Glu Ile Pro Thr Leu Ser Asp Trp Asn Ile Pro Ala
                 85                  90                  95

Gly Asp Glu Val Asp Val Gln Trp Arg Leu Val His Asp Asn Asp Tyr
            100                 105                 110

Phe Ile Lys Pro Val Ser Tyr Leu Ala His Tyr Leu Gly Tyr Ala Trp
        115                 120                 125

Val Gly Gly Asn His Ser Pro Tyr Val Gly Glu Asp Met Asp Val Thr
130                 135                 140

Arg Val Gly Asp Gly Trp Leu Ile Lys Gly Asn Asn Asp Gly Gly Cys
145                 150                 155                 160

Ser Gly Tyr Arg Cys Gly Glu Lys Ser Ser Ile Lys Val Ser Asn Phe
                165                 170                 175

Ser Tyr Thr Leu Glu Pro Asp Ser Phe Ser His Gly Gln Val Thr Glu
            180                 185                 190

Ser Gly Lys Gln Leu Val Lys Thr Ile Thr Ala Asn Ala Thr Asn Tyr
        195                 200                 205

Thr Asp Leu Pro Gln Gln Val Val Val Thr Leu Lys Tyr Asp Lys Ala
    210                 215                 220

Thr Asn Trp Ser Lys Thr Asp Thr Tyr Ser Leu Ser Glu Lys Val Thr
225                 230                 235                 240

Thr Lys Asn Lys Phe Gln Trp Pro Leu Val Gly Glu Thr Glu Leu Ala
                245                 250                 255

Ile Glu Ile Ala Ala Ser Gln Ser Trp Ala Ser Gln Lys Gly Gly Ser
            260                 265                 270

Thr Thr Glu Thr Val Ser Val Glu Ala Arg Pro Thr Val Pro Pro His
        275                 280                 285

Ser Ser Leu Pro Val Arg Val Ala Leu Tyr Lys Ser Asn Ile Ser Tyr
    290                 295                 300

Pro Tyr Glu Phe Lys Ala Glu Val Asn Tyr Asp Leu Thr Met Lys Gly
305                 310                 315                 320

Phe Leu Arg Trp Gly Gly Asn Ala Trp Tyr Thr His Pro Asp Asn Arg
                325                 330                 335

Pro Thr Trp Glu His Thr Phe Arg Leu Gly Pro Phe Arg Gly Gln Gly
            340                 345                 350

Glu Gln His Pro Leu Pro Val Asp Lys Arg Tyr Ile Pro Gly Glu Val
        355                 360                 365

Lys Trp Trp Asp Trp Asn Trp Thr Ile Ser Glu Tyr Gly Leu Ser Thr
    370                 375                 380

Met Gln Asn Asn Leu Gly Arg Val Leu Arg Pro Ile Arg Ser Ala Val
385                 390                 395                 400

Thr Gly Asp Phe Tyr Ala Glu Ser Gln Phe Ala Gly Asp Ile Glu Ile
                405                 410                 415

Gly Gln Pro Gln
            420

<210> SEQ ID NO 15
<211> LENGTH: 422
<212> TYPE: PRT
<213> ORGANISM: Aeromonas hydrophila
```

<400> SEQUENCE: 15

Ala Glu Pro Val Tyr Pro Asp Gln Leu Arg Leu Phe Ser Leu Gly Gln
1               5                   10                  15

Glu Val Cys Gly Asp Lys Tyr Arg Pro Val Asn Arg Glu Glu Ala Gln
            20                  25                  30

Ser Ile Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Ser Ala Ser Ser Thr Trp Cys Tyr Pro Thr Asn Pro
65                  70                  75                  80

Ala Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ser Ile Lys Val Ser Asn Phe Ala
                165                 170                 175

Tyr Asn Leu Asp Pro Asp Ser Phe Lys His Gly Asp Val Thr Gln Ser
        180                 185                 190

Asp Arg Gln Leu Val Lys Thr Val Gly Trp Ala Ile Asn Asp Ser
    195                 200                 205

Asp Thr Pro Gln Ser Gly Tyr Asp Val Thr Leu Arg Tyr Asp Thr Ala
210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Glu Leu Ser
                245                 250                 255

Ile Glu Ile Ala Ala Asn Gln Ser Trp Ala Ser Gln Asn Gly Gly Ser
        260                 265                 270

Thr Thr Thr Ser Leu Ser Gln Ser Val Arg Pro Thr Val Pro Ala His
    275                 280                 285

Ser Lys Ile Pro Val Lys Ile Glu Leu Tyr Lys Ala Asp Ile Ser Tyr
290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
        340                 345                 350

Ser Ser Ile Arg Tyr Gln Trp Asp Lys Arg Tyr Ile Pro Gly Glu Val
    355                 360                 365

Lys Trp Trp Asp Trp Asn Trp Thr Ile Gln Gln Asn Gly Leu Pro Thr
370                 375                 380

Met Gln Asn Asn Leu Ala Lys Val Leu Arg Pro Val Arg Ala Gly Ile
385                 390                 395                 400

-continued

```
Thr Gly Asp Phe Ser Ala Glu Ser Gln Phe Ala Gly Asn Ile Glu Ile
                405                 410                 415

Gly Ala Pro Val Pro Val
            420
```

MUTANT AEROLYSIN AND USES THEREOF

SEQUENCE LISTING

The present application contains a Sequence Listing that has been submitted electronically in ASCII format and is hereby incorporated by reference in its entirety. The ASCII copy, created on Oct. 28, 2020, is named Sequence_listing_PAT7287US00_ST25.txt and is 56,201 bytes in size.

TECHNICAL FIELD

The invention relates to mutant forms of aerolysin. The invention also relates to analyte, polynucleotide or polypeptide transport and characterisation using the mutant forms of aerolysin.

BACKGROUND ART

Using biological nanopores to sequence biopolymers, particularly nucleic acids, was proposed many years ago. Recent advances in enzyme-based control of DNA translocation and in DNA nucleotide resolution using mutated biological pores have satisfied the needs for a functional DNA sequencing biological device.

Nanopore sensing is an approach that relies on the exploitation of individual binding or interaction events between to-be-analysed molecules and pore-forming macromolecules. Nanopore sensors can be created by placing nanometric-scaled pore peptide structures in an insulating membrane and measuring voltage-driven ionic transport through the pore in the presence of substrate molecules. The identity of a substrate can be ascertained through its peculiar electric signature, particularly the duration and extent of current block and the variance of current levels. Two of the essential components of sequencing nucleic acids using nanopore sensing are (1) the control of nucleic acid movement through the pore and (2) the discrimination of nucleotides as the nucleic acid polymer is moved through the pore.

Pore-forming proteins are produced by a variety of organisms and are often involved in defense or attack mechanisms. One notable feature is that they are produced as soluble proteins that subsequently oligomerize and convert into a transmembrane pore in the target membrane. The most extensively characterized pore-forming proteins are the bacterial pore-forming toxins (PFTs), which, depending on the secondary structure elements that cross the bilayer, have been classified as α- or β-PFTs.

In the past, to achieve nucleotide discrimination the nucleic acid has been passed through a mutant of hemolysin (WO 2014/100481). This has provided current signatures that have been shown to be sequence dependent. It has also been shown that a large number of nucleotides contribute to the observed current when a hemolysin pore is used, making a direct relationship between observed current and polynucleotide transportation.

While the current range for nucleotide discrimination has been improved through mutation of the hemolysin pore, a sequencing system would have higher performance if the current differences between nucleotides could be improved further. In addition, it has been observed that when the nucleic acids are moved through a pore, some current states show high variance. It has also been shown that some mutant hemolysin pores exhibit higher variance than others. While the variance of these states may contain sequence specific information, it is desirable to produce pores that have low variance to simplify the system.

In another approach, mutant forms of lysenin, as well as analyte characterisation using thereof, has been described in WO 2013/153359. Lysenin (also known as efLI) is a pore-forming toxin purified from the coelomic fluid of the earthworm *Eisenia fetida*. It specifically binds to sphingomyelin, which inhibits aerolysin-induced hemolysis. In still another approach, mutant forms of the pore-forming Msp monomer, as well as analyte characterisation using thereof, has been described in WO 2012/107778.

There is still a need for rapid and cheap nucleic acid (e.g. DNA or RNA) sequencing technologies across a wide range of applications. Existing technologies are slow and expensive mainly because they rely on amplification techniques to produce large volumes of nucleic acid and require a high quantity of specialist fluorescent chemicals for signal detection. Nanopore sensing has the potential to provide rapid and cheap nucleic acid sequencing by reducing the quantity of nucleotide and reagents required. However, the available nanopore-based solutions for nucleic acid sequencing are still far to be optimized.

Aerolysin, produced by *Aeromonas* species, is the founding member of a large superfamily that spans all of the kingdoms of life. Although it was the first β-PFT for which the X-ray structure of the soluble form was solved, the structure of the pore has remained elusive for long time. Aerolysin forms a heptameric beta-barrel in biological membranes. It is secreted as a monomer that binds to the outer membrane of susceptible cells. Upon binding, the monomers oligomerize to form a water-filled transmembrane channel that facilitates uncontrolled permeation of water, ions, and small organic molecules. Rapid discharge of vital molecules, such as ATP, dissipation of the membrane potential and ionic gradients, and irreversible osmotic swelling leading to rupture or lysis of the cell wall, frequently causing death of the host cell. This pore-forming property has been identified as a major mechanism by which protein toxins cause damage to cells.

Recent studies have demonstrated that aerolysin is a promising candidate to improve the accuracy of DNA sequencing and to develop novel single-molecule proteomic strategies. However, the structure-function relationship between the aerolysin nanopore and its molecular sensing properties remains insufficiently explored, greatly hindering the progress in the development of further biotechnological applications.

Recently, Cao C. et al. (Nat Nanotechnol. Apr. 25, 2016. doi: 10.1038/nnano.2016.66) demonstrated the ability of aerolysin nanopore to resolve at high resolution individual short oligonucleotides that are 2 to 10 bases long without any extra chemicals or modifications, useful for single-molecule analysis of oligonucleotides.

Additionally, Cao C. et al. (Nature Communications volume 9, Article number: 2823, 2018) described nanopore experimental results and molecular simulations based on an aerolysin structural model to map the sensing spots for ssDNA translocation. Computational and experimental results revealed two critical sensing spots (R220, K238) generating two constriction points along the pore lumen. Taking advantage of the sensing spots, all four nucleobases, cytosine methylation and oxidation of guanine can be clearly identified in a mixture sample. However, no rational mutagenesis design of aerolysin to improve its sensing capabilities are described therein.

SUMMARY OF THE INVENTION

The present invention is based at least in part on a series of aerolysin mutants that have been rationally designed and studied, using molecular modelling and simulation based on recent aerolysin structures and models, in order to alter the interaction between an aerolysin monomer and an analyte such as a polynucleotide, polypeptide or small molecules such as ions. This region corresponds to position 207 to position 290 of SEQ ID NO: 1. The invention concerns mutant monomers in which one or more modifications into the identified region aim to improve the ability of the monomer to interact with an analyte. Pores comprising the novel mutant monomers have an enhanced ability to interact with a substrate analyte such as polynucleotides, polypeptide and small molecules, and therefore display improved properties for estimating the characteristics of, such as the sequence of, polynucleotides. The aim of this aerolysin mutation process is to increase a current blockage difference/variance (with respect to the basal current of the open pore) in order to better discriminate different bases in a nanopore sensing approach. A so designed aerolysin pore is able to translocate very long, up to thousands bases, single strand nucleic acid stretches for better sequencing, reason why the velocity of translocation should be in the order of few nucleotides per millisecond to allow a better discrimination of the sequence.

In some implemented embodiments, aerolysin mutants were expressed, purified and reconstituted in lipid bilayer membranes for single-channel recording and molecular translocation experiments. By full integration of computational and experimental data, it was understood how the ionic conductance, ion selectivity and translocation properties of the aerolysin pore are controlled at the molecular level. Particularly, the dwell time of molecular translocation has been shown to be correlated to the diameter of the narrowest constriction of the aerolysin pore, demonstrating the importance of steric hindrance for molecular translocation. Altogether, the sensing determinants of aerolysin are mainly controlled by residues at the distinctive double β-barrel cap, thus that any modification of the pore needs to preserve this unique sensing structure.

Accordingly, provided herein in certain aspects is a polypeptide comprising a modified aerolysin amino acid sequence comprising one or more amino acid substitutions at one or more positions corresponding to positions 207-290 of the amino acid sequence of SEQ ID NO: 1 (also referred to herein as "mutant aerolysin"). Particularly, one aspect of the invention provides for a polypeptide comprising a modified aerolysin amino acid sequence, wherein said sequence comprises the amino acid sequence of SEQ ID NO: 1 having one or more amino acid substitutions at one or more positions corresponding to positions 220, 238, 242 and 282. In some additional or alternative embodiments, polypeptides according to the invention further comprises one or more amino acid substitutions at one or more positions corresponding to positions 209, 216, 222, 244, 246, 252, 254 and 258 of SEQ ID NO: 1 with the proviso that said one or more amino acid substitutions are not D209R, Q212R, R282G, N226Q, K238F, K238G, K238Y, K238C, T232K, Q212R, R282G, D209R, N226Q.

A modified aerolysin polypeptide generally comprises, consists essentially of or consists of a modified aerolysin amino acid sequence. An amino acid sequence of a wild-type (i.e., native, unmodified) aerolysin monomer polypeptide from *Aeromonas hydrophila* is provided herein as SEQ ID NO: 1. Such modifications alter the ability of the aerolysin monomer, assembled in a heptameric pore form, to interact with a polymer such as a polynucleotide, a polypeptide or even another analyte via (i) a steric effect of the aerolysin pore on the interacting substrate, (ii) a net charge alteration of the aerolysin pore and/or (iii) the ability of the aerolysin pore to alter the hydrogen bonds established with an interacting substrate.

In particular, a mutant aerolysin pore according to the present invention comprises one or more modifications on the aerolysin monomer sequence that change the net positive charge, as well as the size of the pore region formed upon oligomerization of the monomers into a pore-forming structure. Said net charge is increased by e.g. introducing one or more positively charged amino acids and/or by neutralising one or more negative charged amino acids, for instance by substituting one or more negatively charged amino acids with one or more uncharged amino acids, non-polar amino acids and/or aromatic amino acids or by introducing one or more positive charged amino acids adjacent to one or more negatively charged amino acids. The size of the pore is altered by increasing or reducing the steric hindrance of side-chain protruding to the internal lumen of the pore.

In particular, a mutant aerolysin monomer having a modified aerolysin amino acid sequence according to the invention comprises a substitution on at least one of the following positions of SEQ ID NO: 1: 209, 220, 238, 242, 282, 216, 222, 244, 246, 252, 254 and 258 with the proviso that said one or more amino acid substitutions are not Q212R, R282G, N226Q, K238F, K238G, K238Y, K238C, T232K, Q212R, R282G, D209R, N226Q.

Preferably, the amino acid(s) are substituted into the mutant aerolysin monomer at positions R220, K238, K242, R282, D209, D216, D222, K244, K246, E252, E254 and E258, wherein the amino acid(s) substituted into the mutant aerolysin monomer at positions R220, K238, K242 and R282 are selected from the group comprising at least one asparagine (N), glutamine (Q), arginine (R), glutamic acid (E), leucine (L), lysine (K), tryptophan (W), histidine (H) or alanine (A), and wherein the amino acid(s) substituted into the mutant aerolysin monomer at positions D216, D222, K244, K246, E252, E254 and E258 are selected from the group comprising at least one asparagine (N), serine (S), glutamine (Q), arginine (R), glycine (G), tyrosine (Y), aspartic acid (D), glutamic acid (E), leucine (L), lysine (K), cysteine (C) or alanine (A) and wherein the amino acid(s) substituted into the mutant aerolysin monomer at position D209 is selected from the group comprising at least one asparagine (N), serine (S), glutamine (Q), glycine (G), tyrosine (Y), aspartic acid (D), glutamic acid (E), leucine (L), lysine (K), cysteine (C) or alanine (A) with the proviso that said one or more amino acid substitutions are not Q212R, R282G, N226Q, K238F, K238G, K238Y, K238C, T232K, Q212R, R282G, D209R, N226Q.

According to another embodiment, the amino acid(s) are substituted into the mutant aerolysin monomer at positions R220, K238, K242 and R282 are selected from the group comprising asparagine (N), glutamine (Q), arginine (R), glutamic acid (E), leucine (L), lysine (K), tryptophan (W), histidine (H) or alanine (A).

In preferred embodiments, a mutant aerolysin monomer according to the invention comprises at least one of the following mutations: R220A/W/K/E/Q, R282A/W, K238A/Q/N/R/W/E, K242A/W as well as any combination thereof.

Preferably, the amino acid(s) substituted into the mutant aerolysin monomer at positions D216, D222, D222, K244, K246, E252, E254 and E258 are selected from the group comprising asparagine (N), serine (S), glutamine (Q), arginine (R), glycine (G), tyrosine (Y), aspartic acid (D), glutamic acid (E), leucine (L), lysine (K), cysteine (C) or alanine (A) and even more preferably from the group comprising asparagine (N), glutamine (Q), arginine (R), aspartic acid (D) or alanine (A).

In preferred embodiments, a mutant aerolysin monomer according to the invention comprises at least one of the following mutations: R220A/W/K/Q/E, R282A/E/W, K238A/Q/N/R/W/H/E, K242A/W, D216A/N/R/Q, D222A/N/R/Q, K244A/N/R/Q/D, K246A/N/R/Q/D, E252A/N/R/Q, E254A/N/R/Q, E258A/N/R/Q, D209K/A/N/Q/E/C/S/G/Y/D/L as well as any combination thereof and even more preferably comprises at least one of the following mutations: D216A/N/Q/R, D222A/N/Q/R, K244A/N/Q/R/D, K246A/N/Q/R/D, E252A/N/Q/R, E254A/N/Q/R, E258A/N/R/Q, D209K as well as any combination thereof.

In embodiments of the invention, a mutant aerolysin monomer according to invention comprises a substitution on at least one of the following positions of SEQ ID NO: 1: 220, 238, 242 and 282 (hereinafter referred to "group 1 of mutations") together with a substitution on at least one of the following positions 209, 216, 222, 244, 246, 252, 254 and 258 (hereinafter referred to "group 2 of mutations"). For example, a mutant aerolysin monomer according to the invention comprises at least one of the following mutations in group 1 of mutations: R220A/W/K/Q, R282A/E/W, K238A/Q/N/R/W/H, K242A/W, as well as at least one of the following mutations in group 2 of mutations: D216A/N/Q/R, D222A/N/Q/R, K244A/N/Q/R/D, K246A/N/Q/R/D, E252A/N/Q/R, E254A/N/Q/R, E258A/N/R/Q, D209K/A/N/Q/E/C/S/G/Y/D/L as well as any combination thereof.

The invention also provides:

A mutant aerolysin pore comprising at least one polypeptide of SEQ ID NO: 8 or a variant thereof having one or more amino acid substitutions at one or more positions corresponding to positions 220, 238, 242, 282, 209, 216, 222, 244, 246, 252, 254 and 258 with the proviso that said one or more amino acid substitutions are not Q212R, R282G, N226Q, K238F, K238G, K238Y, K238C, T232K, Q212R, R282G, D209R, N226Q.

A construct comprising:

a) two or more covalently attached monomers derived from said mutant aerolysin monomer;

b) a homo-oligomeric pore derived from said mutant aerolysin monomer comprising identical mutant monomers; or c) a hetero-oligomeric pore derived from said mutant aerolysin monomer as described herein, wherein at least one of the monomers differs from the others.

A method of sensing and/or characterising a target substrate comprising:

(a) contacting the target substrate with the mutant aerolysin pore of the invention so to allow the movement of the target substrate through said pore and a portion of the substrate interacts with said pore; and (b) measuring a current passing through said pore, thereby sensing and/or characterising the target substrate. In some embodiments, steps (a) and (b) are carried out with a voltage applied across the pore. Preferably, the target substrate is a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant.

In some embodiments, the substrate is a nucleic acid, and said contacting is controlled by handling enzyme so that the movement of the nucleic acid through the pore and a proportion of the nucleotides in the target sequence interacts with the pore. In one embodiment, the step of characterising a target polynucleotide comprises estimating the sequence of, or sequencing the, target polynucleotide; and an apparatus for sensing a target substrate in a sample, comprising a mutant aerolysin pore according to the invention, wherein in some embodiments the target substrate is a nucleic acid sequence, further comprising a nucleic acid handling enzyme. Also provided is a system comprising a membrane having at least one mutant aerolysin pore according to the invention spanning across the membrane thickness.

Further embodiments of the present invention are defined by the appended claims.

The above and other objects, features and advantages of the herein presented subject-matter will become more apparent from a study of the following description with reference to the attached figures showing some preferred aspects of said subject-matter.

DESCRIPTION OF THE FIGURES

FIG. 1 shows the structural characterization of aerolysin nanopore variants. (a) Structural model of aerolysin nanopore based on cryo-EM data. The amino acids at the sensing regions are marked as R282, R220, K238 and K242. MD simulations were performed on a truncated pore model (i.e., residues 195-300 and 409-424, highlighted in solid dark grey). Here a typical simulation system is represented with positive applied voltage, i.e. a negative potential is applied at the cap side (cis) and a positive potential at the stem side (trans). The bottom of the pore is used as reference 0 Å distance in all the graphs. (b) Top view of the wt and mutants pore lumen. For wt, the view is focused at R220, and for the mutants, at the mutated region. (c) The diameter of wt and engineered aerolysin nanopores calculated with the PoreWalker server. Distance ~88.5 Å represents the R282 position at the cap region, while a distance of ~73.5 Å indicates R220 also at the cap; ~22.5 Å corresponds to K238 at the stem, and ~10.5 Å is the K242 position also at the stem region. Each point represents the mean value±st. dev. of at least ten distinct structures extracted from MD simulations. (d) Calculated diameter of the various mutants at the two main sensing regions for 220 (circles) and 238 (triangles) position;

FIG. 2 shows the open pore current and ion selectivity of aerolysin mutants. (a) Simulated open pore current at +150 mV in wt and engineered aerolysin pores. (b) Current-voltage relationships in aerolysin wt and mutants nanopores, where each point represents the mean value±st. dev. of at least five independent experiments. (c) Comparison of open pore current at +150 mV calculated by MD simulations (circles) with that obtained by single-channel experiments (triangles). (d) The calculation of $I_{Cl}$ (triangles) and $I_K$ (squares) in various engineered nanopores at 1.0 M solution of KCl electrolyte. At positive voltage, $I_{Cl}$ and $I_K$ are represented with solid triangles and squares, respectively, while shown with the open triangles and squares under negative voltages. (e) The averaged density of $Cl^-$ in wt (squares), R220Q (circles), and R220E (triangles) at +150 mV along the z axis of the pore, as defined by the local radii profile during 200 ns MD simulation. (f) The density of $Cl^-$ in wt (squares), K238Q (circles), and K238E (tringles) at −150 mV;

FIG. 3 shows DNA sensing by various engineered pores. (a) Structure of $dA_4$ with its electrostatic potential mapped on the molecular surface. (b) Raw single-channel recording traces upon $dA_4$ addition into the cis chambers of wt, R282A, R220A, R220W, K238A, K238Q, K238N and K238R mutants, respectively. The final concentration of dA$_4$ in the chamber was 2.0 µM. (c) Dwell time distribution of dA$_4$ events of the wt, R220A, R220W, K238A, K238Q, K238N and K238R mutants under +100 mV voltage. (d) Comparison between dwell time of dA$_4$ (triangles) and the pore diameter at the R220 (black circles) and K238 (grey circles) regions. (e) Electrostatic potential maps of wt, R282A, R220A, R220W, K238A, K238Q, K238N and K238R along the pore lumen. The lipid membrane region is represented by a grey shadow;

FIG. 4 shows the negatively charged peptide sensing by aerolysin engineered pores. (a) 3D structure of EYQ3 with its electrostatic potential mapped on the peptide molecular surface. (b) Raw single-channel recording traces upon EYQ3 addition into the cis chamber of wt, K238A, K238Q, K238N and K238R mutants, respectively. The final concentration of EYQ3 in the chamber was 2 µM. (c) Dwell time distribution of EYQ3 crossing through the wt, K238A, K238Q, K238N and K238R protein pores under +100 mV voltage. (d) Comparison between dwell time of EYQ3 (squares), dwell time of DNA (triangles), and the diameter at R220 region (circles) for wt and pore mutants;

FIG. 5 shows the positively charged peptide sensing by various engineering pores. (a) 3D structure of HIV-1 Tat (47-57) (PDB:1TAC) with its electrostatic potential mapped on the peptide molecular surface. (b) Raw single-channel recording traces upon HIV-1 Tat (47-57) addition into the cis side of the chamber for wt, R282A, R220A, or R220W, respectively. The final concentration of HIV-1 Tat (47-57) in the chamber was 2 µM. (c) Inter-event interval (Ton) distribution of HIV-1 Tat translocation on the R282A (black), R220A (dark grey) and R220W (grey) pore mutants. The values were determined by the single exponential fitting. Relative dwell times are reported in FIG. 7. (d) Raw current traces of HIV-1 Tat (47-57) translocation through R220W at different voltages ranging (from −60 mV to −100 mV). (e) Comparison between dwell time of HIV-1 Tat (47-57) peptide (squares) and the diameter of R220 (circles) and K238 (circles) region;

DETAILED DESCRIPTION OF THE INVENTION

Figure 1:
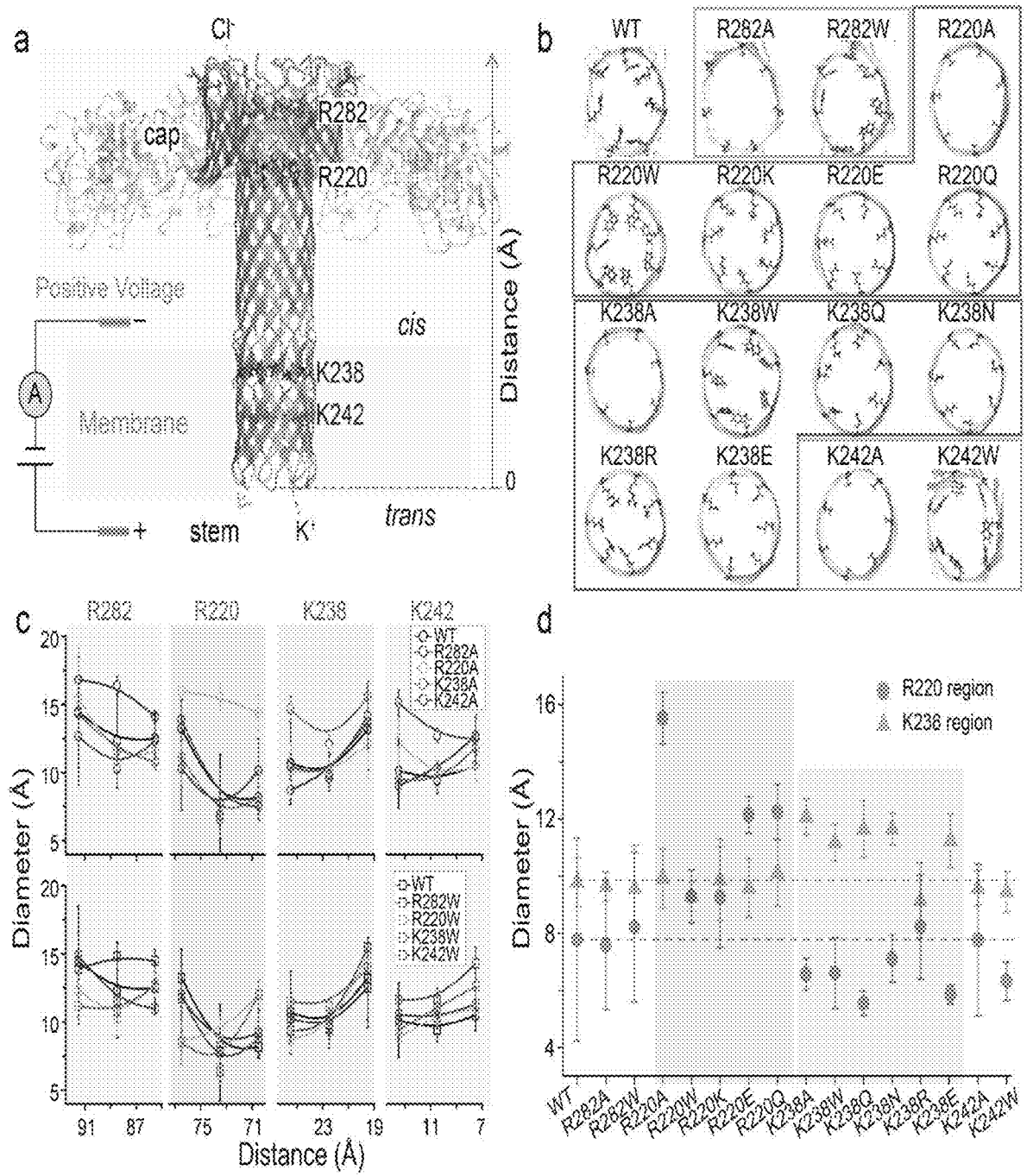

The subject matter herein described will be clarified by means of the following description. It is however to be understood that the subject matter described in this specification is not limited to the aspects described herein and depicted in the drawings; to the contrary, the scope of the subject-matter herein described is defined by the claims. Moreover, it is to be understood that the specific conditions or parameters described and/or shown in the following are not limiting of the subject matter herein described, and that the terminology used herein is for the purpose of describing particular aspects by way of example only and is not intended to be limiting.

Unless otherwise defined, technical and scientific terms used herein have the same meaning as commonly understood by one of ordinary skill in the art to which this invention belongs. Further, unless otherwise required by the context, singular terms shall include pluralities and plural terms shall include the singular. The methods and techniques of the present disclosure are generally performed according to conventional methods well known in the art and as described in various general and more specific references that are cited and discussed throughout the present specification unless otherwise indicated. Further, for the sake of clarity, the use of the term "about" is herein intended to encompass a variation of +/−10% of a given value.

As used in the following and in the appended claims, the singular forms "a", "an" and "the" include plural referents unless the context clearly dictates otherwise. Also, the use of "or" means "and/or" unless stated otherwise. Similarly, "comprise", "comprises", "comprising", "include", "includes" and "including" are interchangeable and not intended to be limiting. It is to be further understood that where for the description of various embodiments use is made of the term "comprising", those skilled in the art will understand that in some specific instances, an embodiment can be alternatively described using language "consisting essentially of" or "consisting of."

Mutant Aerolysin Monomers

The present invention provides mutant aerolysin monomers. The mutant aerolysin monomers may be used to form the pores of the invention. A mutant aerolysin monomer is a monomer whose sequence varies from that of a wild-type mature aerolysin monomer (i.e. SEQ ID NO: 1) and which retains the ability to form a pore in the presence of other monomers of the invention or other monomers from aerolysin or derived from aerolysin. Methods for confirming the ability of mutant monomers to form pores are well-known in the art and are discussed in more detail below.

The mutant monomers have an altered ability to interact with a substrate such as a nucleotide, an oligonucleotide, a polynucleotide, a peptide, a polypeptide or an ion. Pores comprising one or more of the mutant monomers, or preferably one or more polypeptide derived from the mutant monomers (e.g. a monomer having the sequence disclosed in SEQ ID NO: 8, representing the mature aerolysin monomer without a C-terminal propeptide) therefore have improved substrate reading properties e.g. display (1) improved substrate capture and/or (2) improved substrate recognition or discrimination. In particular, pores constructed from mutant monomers easily capture and efficiently translocate at optimal rate (i.e., few nucleotides per millisecond, such as 2, 3, 4, 5, 6, 7, 8, 9, or 10 nucleotides per millisecond) nucleotides and polynucleotides compared to the wild type pore form, and/or are able to better discriminate different nucleotides or substrates in general. The same is true, mutatis mutandis, for other substrates such as peptides/polypeptides.

In addition, pores constructed from mutant monomers display a varied, such as increased, current range, which makes it easier to discriminate between different nucleotides or amino acids, and a reduced variance of states, which increases the signal-to-noise ratio. In addition, the number of nucleotides contributing to the current as the polynucleotide moves through pores constructed from the mutants is decreased. This makes it easier to identify a direct relationship between the observed current as the polynucleotide or polypeptide moves through the pore, and the polynucleotide or polypeptide itself.

The improved substrate reading properties of the mutants are achieved via five main mechanisms, namely by changes in the:
  steric (increasing or decreasing the size of amino acid residues);
  charge (e.g. introducing or removing negative charges and/or introducing or removing positive charges);

hydrogen bonding (e.g. introducing amino acids that can create hydrogen bond to the substrate or portions thereof, such as base pairs);

pi stacking (e.g. introducing amino acids that interact through delocalised electron pi systems); and/or alteration of the structure of the pore (e.g. introducing amino acids that increase or reduce the size of the barrel or channel).

Any one or more of these five mechanisms may be responsible for the improved properties of the pores formed from the mutant monomers of the invention. For instance, a pore comprising a mutant monomer of the invention may display improved nucleotide reading properties as a result of altered steric/structure, altered hydrogen bonding and an altered charge.

A mutant monomer of the invention comprises a variant of the sequence shown in SEQ ID NO: 1. SEQ ID NO: 1 is the wild-type sequence of the mature (i.e. without a signal peptide) aerolysin monomer. A variant of SEQ ID NO: 1 is a polypeptide that has an amino acid sequence which varies from that of SEQ ID NO: 1 and which retains its ability to form a pore.

The inventors have identified a region within the aerolysin monomer which can be modified to likely alter the interaction between a monomer and a substrate such as a polynucleotide or a polypeptide, such as when the polynucleotide or polypeptide is characterised using nanopore sensing with a pore comprising the monomer. The identified region spans from about position 207 to about position 290 of SEQ ID NO: 1. At least a part of this region typically contributes to the membrane spanning region of aerolysin. At least a part of this region typically contributes to the barrel or channel of aerolysin. At least a part of this region typically contributes to the internal wall or lining of aerolysin.

Information on the structural features of the aerolysin monomer in all its states and the pore obtainable therefrom can be retrieved on the website http://www.uniprot.org/, access number P09167, and previously described in literature in e.g. Degiacomi M. T. et al., Nat Chem Biol. 2013 October; 9(10):623-9.

In accordance with the invention, the variant comprises one or more modifications within the region of from about position 207 to about position 290 of SEQ ID NO: 1 which alter the ability of the monomer, and/or the region, to interact with a substrate such as a polynucleotide, a polypeptide or a molecular analyte. In particular, the variant comprises at least one modification at positions 220, 238, 242, 282, 209, 216, 222, 244, 246, 252, 254 and 258 of SEQ ID NO: 1 with the proviso that said modification is not Q212R, R282G, N226Q, K238F, K238G, K238Y, K238C, T232K, Q212R, R282G, D209R, N226Q.

The interaction between the monomer and a substrate such as a polynucleotide is in general tailored so to optimize the "reading" properties of the pores of the invention in a nanopore sensing approach. An ameliorated interaction between the monomer and e.g. a polynucleotide will, for example, facilitate capture of the polynucleotide by pores comprising the mutant monomer thanks to an improved electrostatic pairing, or will, for example, improve recognition or discrimination of the polynucleotide thanks to steric modulations to optimize the pore size and/or optimization of charges. The same concept is true also for other analytes or substrates such as, and non-limited to, ions or polypeptide.

The invention therefore provides a mutant aerolysin monomer comprising a variant of the sequence shown in SEQ ID NO: 1, wherein the monomer is capable of forming a pore and wherein the variant comprises one or more modifications from about position 207 to about position 290 of SEQ ID NO: 1 which alter the ability of the monomer to interact with a target analyte such as a polynucleotide. In particular, the variant comprises at least one modification at positions 220, 238, 242, 282, 209, 216, 222, 244, 246, 252, 254 and 258 of SEQ ID NO: 1 with the proviso that said one or more modification is not Q212R, R282G, N226Q, K238F, K238G, K238Y, K238C, T232K, Q212R, R282G, D209R, N226Q.

As it will be evident to a person skilled in the relevant art, the ability of the monomer of the invention to form a pore, as for many other similar pore-forming polypeptides, derives from its structure and the presence of suitable, e.g. physiological, homo-hetero oligomerization conditions. In particular, the aerolysin monomers, both in the wild-type and in the mutated form, undergo a maturation/folding process that foresees several passages. Aerolysin is produced as an inactive precursor, proaerolysin, which contains a C-terminal peptide (CTP) required for folding into its soluble form. Proteolysis in the loop that connects the CTP to the main body allows aerolysin to oligomerize in a heptameric ring-like complex that inserts into the target membrane to form the pore. It is therefore herein tacitly understood that, when referring to a formed pore, the monomer of the invention comprises, consists of or substantially consists of a polypeptide having the sequence shown in SEQ ID NO: 8, i.e. the mature aerolysin monomer without an N-terminal signal peptide and without a C-terminal propeptide, and which substantially differs from the sequence shown in SEQ ID NO: 1 in the C-terminal domain. "Substantially" herein means that, upon alignment of SEQ ID NO: 1 with a sequence comprising SEQ ID NO: 8, no more than five consecutive amino acid residues in the CTP must be equal.

The same is also true for homologues or paralogues of the aerolysin monomer having the sequence shown in SEQ ID NO: 1, namely polypeptides shown in SEQ ID NOs: 2 to 7, for which the correspondent mature (i.e. without a CTP) sequences are shown in SEQ ID NOs: 10 to 15.

The ability of the monomer to interact with a substrate such as a polynucleotide can be determined using methods that are well-known in the art. The monomer may interact with a substrate in any way, e.g. by non-covalent interactions, such as hydrophobic interactions, hydrogen bonding, Van der Waal's forces or electrostatic forces. For instance, the ability of the region to bind to a polynucleotide can be measured using a conventional binding assay.

Suitable assays include, but are not limited to, fluorescence-based binding assays, nuclear magnetic resonance (NMR), Isothermal Titration calorimetry (ITC) or Electron spin resonance (ESR) spectroscopy.

Modifications of protein nanopores that alter their ability to interact with a polynucleotide, in particular improve their ability to capture and/or recognise or discriminate polynucleotides, are well documented in the art. For instance, such modifications are disclosed in WO 2010/034018 and WO 2010/055307. Similar modifications can be made to the aerolysin monomer in accordance with this invention.

Any number of modifications may be made, such as 1, 2, 3, 4, 5, 10, 15, 20, 30, 50 or more modifications. Any modification(s) can be made as long as the ability of the monomer to interact with a polynucleotide is altered. Suitable modifications include, but are not limited to, amino acid substitutions, amino acid additions and amino acid deletions. The one or more modifications are preferably one or more substitutions. This is discussed in more detail below.

The one or more modifications preferably (a) alter the steric effect of the monomer, or preferably alter the steric effect of the region, (b) alter the net charge of the monomer, or preferably alter the net charge of the region, (c) alter the ability of the monomer, or preferably of the region, to hydrogen bond with the polynucleotide and/or (d) alter the structure of the monomer, or preferably alter the structure of the region. Any combination of the above can be envisaged in the frame of the present disclosure.

For (a), the steric effect of the monomer can be increased or decreased. Any method of altering the steric effects may be used in accordance with the invention. The introduction of bulky residues, such as phenylalanine (F), tryptophan (W), tyrosine (Y), histidine (H), Leucine (L) or Isoleucine (I) typically increases the steric of the monomer. The one or more modifications are preferably the introduction of one or more of F, W, Y, H, L and I. Any combination of F, W, Y, H, L and I may be introduced. The one or more of F, W, Y, H, L and I may be introduced by addition. The one or more of F, W, Y, H, L and I are preferably introduced by substitution.

The removal of bulky residues, such as phenylalanine (F), tryptophan (W), tyrosine (Y) or histidine (H), conversely typically decreases the steric of the monomer. The one or more modifications are preferably the removal of one or more of F, W, Y and H. Any combination of F, W, Y and H may be removed. The one or more of F, W, Y and H may be removed by deletion. The one or more of F, W, Y and H are preferably removed by substitution with residues having smaller side groups, such as serine (S), threonine (T), alanine (A) and valine (V).

For (b), the net charge can be altered in any way. The net positive charge is preferably increased or decreased. The net positive charge can be increased in any manner. The net positive charge is preferably increased by introducing, preferably by substitution, one or more positively charged amino acids and/or neutralising, preferably by substitution, one or more negative charges.

The net positive charge is preferably increased by introducing one or more positively charged amino acids. The one or more positively charged amino acids may be introduced by addition. The one or more positively charged amino acids are preferably introduced by substitution. A positively charged amino acid is an amino acid with a net positive charge. The positively charged amino acid(s) can be naturally-occurring or non-naturally-occurring. The positively charged amino acids may be synthetic or modified. For instance, modified amino acids with a net positive charge may be specifically designed for use in the invention. A number of different types of modification to amino acids are well known in the art.

Naturally-occurring positively charged amino acids include, but are not limited to, histidine (H), lysine (K) and arginine (R). The one or more modifications are typically the introduction of one or more of H, K and R. Any number and combination of H, K and R may be introduced. The one or more of H, K and R may be introduced by addition. The one or more of H, K and/or R are preferably introduced by substitution. Suitable positions for the introduction of such residues are discussed in more detail below.

Methods for adding or substituting naturally-occurring amino acids are well known in the art. For instance, methionine (M) may be substituted with arginine (R) by replacing the codon for methionine (ATG) with a codon for arginine (AGA) at the relevant position in a polynucleotide encoding the monomer. The polynucleotide can then be expressed as discussed below.

Methods for adding or substituting non-naturally-occurring amino acids are also well known in the art. For instance, non-naturally-occurring amino acids may be introduced by including synthetic aminoacyl-tRNAs in the IVTT system used to express the pore. Alternatively, they may be introduced by expressing the monomer in E. coli that are auxotrophic for specific amino acids in the presence of synthetic (i.e. non-naturally-occurring) analogues of those specific amino acids. They may also be produced by naked ligation if the pore is produced using partial peptide synthesis.

Any amino acid may be substituted with a positively charged amino acid. One or more uncharged amino acids, non-polar amino acids and/or aromatic amino acids may be substituted with one or more positively charged amino acids. Uncharged amino acids have no net charge.

Suitable uncharged amino acids include, but are not limited to, cysteine (C), serine (S), threonine (T), methionine (M), asparagine (N) and glutamine (Q).

Non-polar amino acids have non-polar side chains. Suitable non-polar amino acids include, but are not limited to, glycine (G), alanine (A), proline (P), isoleucine (I), leucine (L) and valine (V).

Aromatic amino acids have an aromatic side chain. Suitable aromatic amino acids include histidine (H), phenylalanine (F), tryptophan (W) and tyrosine (Y). Preferably, one or more negatively charged amino acids are substituted with one or more positively charged amino acids. Suitable negatively charged amino acids include, but are not limited to, aspartic acid (D) and glutamic acid (E).

Any number of positively charged amino acids may be introduced or substituted. For instance, 1, 2, 3, 4 5, 10, 15, 20, 25, 30 or more positively charged amino acids may be introduced or substituted.

The net positive charge may be increased by neutralising one or more negative charges. The one or more negative charges may be neutralised by replacing by substitution one or more negatively charged amino acids with one or more uncharged amino acids, non-polar amino acids and/or aromatic amino acids. The removal of negative charge increases the net positive charge. The uncharged amino acids, non-polar amino acids and/or aromatic amino acids can be naturally-occurring or non-naturally-occurring. They may be synthetic or modified. Suitable uncharged amino acids, non-polar amino acids and aromatic amino acids are discussed above.

Any number and combination of uncharged amino acids, non-polar amino acids and/or aromatic amino acids may be substituted. For instance, 1, 2, 3, 4, 5, 10, 15, 20, 25, or 30 or more uncharged amino acids, non-polar amino acids and/or aromatic amino acids may be substituted. Negatively charged amino acids may be substituted with (1) uncharged amino acids; (2) nonpolar amino acids; (3) aromatic amino acids; (4) uncharged amino acids and non-polar amino acids; (5) uncharged amino acids and aromatic amino acids; and (5') non-polar amino acids and aromatic amino acids; or (6) uncharged amino acids, non-polar amino acids and aromatic amino acids.

The one or more negative charges may be neutralised by introducing one or more positively charged amino acids near to, such as within 1, 2, 3 or 4 amino acids, or adjacent to one or more negatively charged amino acids. Examples of positively and negatively charged amino acids are discussed above. The positively charged amino acids may be introduced in any manner discussed above, for instance by substitution.

The net positive charge may be decreased by introducing one or more negatively charged amino acids and/or neutralising one or more positive charges. Ways in which this might be done will be clear from the discussion above with reference to increasing the net positive charge. All of the embodiments discussed above with reference to increasing the net positive charge equally apply to decreasing the net positive charge except the charge is altered in the opposite way. In particular, the one or more positive charges may be neutralised by substituting one or more positively charged amino acids with one or more uncharged amino acids, non-polar amino acids and/or aromatic amino acids or by introducing one or more negatively charged amino acids near to, such as within 1, 2, 3 or 4 amino acids distant from, a positively charged amino acid, or sterically adjacent to one or more positively charged amino acids.

The net negative charge can be increased or decreased. All of the embodiments discussed above with reference to increasing or decreasing the net positive charge equally apply to decreasing or increasing the net negative charge respectively.

For (c), the ability of the monomer to hydrogen bond may be altered in any manner. The introduction of serine (S), threonine (T), asparagine (N), glutamine (Q), tyrosine (Y) or histidine (H) increases the hydrogen bonding ability of the monomer. The one or more modifications are preferably the introduction of one or more of S, T, N, Q, Y and H. Any combination of S, T, N, Q, Y and H may be introduced. The one or more of S, T, N, Q, Y and H may be introduced by addition. The one or more of S, T, N, Q, Y and H max be introduced by substitution. Suitable positions for the introduction of such residues are discussed in more detail below.

The removal of serine (S), threonine (T), asparagine (N), glutamine (Q), tyrosine (Y) or histidine (H) decreases the hydrogen bonding ability of the monomer. The one or more modifications may be the removal of one or more of S, T, N, Q, Y and H. Any combination of S, T, N, Q, Y and H may be removed. The one or more of S, T, N, Q, Y and H may be removed by deletion. The one or more of S, T, N, Q, Y and H may be removed by substitution with other amino acids which hydrogen bond less well, such as alanine (A), valine (V), isoleucine (I) and leucine (L).

For (d), one or more modifications made in accordance with the invention which alter the structure of the monomer. For example, one or more loop regions can be removed, shortened or extended. This typically facilitates the entry or exit of a polynucleotide into or out of the pore. The one or more loop regions may be the cis side of the pore, the trans side of the pore or on both sides of the pore. Alternatively, one or more regions of the amino terminus and/or the carboxy terminus of the pore can be extended or deleted. This typically alters the size and/or charge of the pore.

It will be clear from the discussion above that the introduction of certain amino acids will enhance the ability of the monomer to interact with a polynucleotide via more than one mechanism. For instance, the substitution of E with Q will not only increase the net positive charge (by neutralising negative charge) in accordance with (b), but will also increase the ability of the monomer to hydrogen bond in accordance with (c).

In accordance to the invention, the variant comprises a substitution of one or more amino acids comprised into group 1 of mutations, namely at least at one or more of the following positions of SEQ ID NO: 1 comprising positions: 220, 238, 242 or 282. The variant preferably comprises a substitution at 1, 2, 3 or 4 of those positions.

The amino acids substituted into the variant may be naturally-occurring or non-naturally occurring derivatives thereof. Any position of group 1 of mutations may be substituted with asparagine (N), serine (S), glutamine (Q), arginine (R), glycine (G), tyrosine (Y), aspartic acid (D), glutamic acid (E), leucine (L), lysine (K), cysteine (C) or alanine (A), preferably with asparagine (N), glutamine (Q), arginine (R), glutamic acid (E), leucine (L), lysine (K), cysteine (C), tryptophan (W) or alanine (A).

The variant most preferably comprises at least one of the following mutations of SEQ ID NO: 1:
  (a) alanine (A) or lysine (K) or tryptophan (W) or glutamine (Q) at position 220;
  (b) alanine (A) or glutamine (Q) or asparagine (N) or arginine (R) or tryptophan (W) at position 238, preferably alanine and glutamine;
  (c) alanine (A) or tryptophan (W) at position 242, preferably alanine;
  (d) alanine (A) or glutamic acid (E) or tryptophan (W) at position 282.

The variant may include any number of mutations (a) to (d), such as 1, 2, 3 or 4 of the mutations.

In accordance to the invention, the variant comprises a substitution of one or more amino acids comprised into group 2 of mutations, namely at least at one or more of the following positions of SEQ ID NO: 1: 209, 216, 222, 244, 246, 252, 254 or 258 with the proviso that said one or more amino acid substitution is not Q212R, R282G, N226Q, K238F, K238G, K238Y, K238G, T232K, Q212R, R282G, D209R, N226Q. The variant preferably comprises a substitution at 1, 2, 3, 4, 5, 6 or 7 of those positions.

The amino acids substituted into the variant may be naturally-occurring or non-naturally occurring derivatives thereof. Any position of group 2 of mutations may be substituted with asparagine (N), serine (S), glutamine (Q), arginine (R), glycine (G), tyrosine (Y), aspartic acid (D), glutamic acid (E), leucine (L), lysine (K), cysteine (C) or alanine (A), preferably with asparagine (N), glutamine (Q), or alanine (A), arginine (R), aspartic acid (D) and serine (S) with the proviso that said one or more amino acid substitution is not Q212R, R282G, N226Q, K238F, K238G, K238Y, K238G, T232K, Q212R, R282G, D209R, N226Q.

The choice of the mutants according to the invention depends on the aim of the sensing/analysis of a target analyte of interest; for instance, amino acids at the entrance of aerolysin pore (e.g. amino acids at positions 282, 216, 220, 222) alter capturing ability of the detected molecules. Therefore, preference depend on the target molecules. For example, R282A aerolysin mutants show good capability of capturing positively charged peptides, while D216A aerolysin mutants performs better for negatively charged peptides/DNA sensing.

The variant preferably comprises at least one of the following mutations of SEQ ID NO: 1:
  (a) alanine (A) or asparagine (N) or arginine (R) or glutamine (Q) at position 216;
  (b) alanine (A) or asparagine (N) or arginine (R) or glutamine (Q) at position 222;
  (c) alanine (A) or asparagine (N) or aspartic acid (D) or glutamic acid (E) or glutamine (Q) at position 244, preferably alanine or asparagine or aspartic acid;
  (d) alanine (A) or asparagine (N) or aspartic acid (D) or glutamic acid (E) or glutamine (Q) at position 246, preferably alanine or asparagine or aspartic acid;
  (e) alanine (A) or asparagine (N) or arginine (R) or glutamine (Q) at position 252, preferably asparagine, arginine and glutamine;
  (f) alanine (A) or asparagine (N) or arginine (R) or glutamine (Q) at position 254, preferably asparagine, arginine and glutamine;

(g) alanine (A) or asparagine (N) or arginine (R) or glutamine (Q) at position 258, preferably asparagine, arginine and glutamine;

The variant may include any number of mutations (a) to (g), such as 1, 2, 3, 4, 5, 6 or 7 of the mutations.

According to some embodiments of the invention, the variant comprises a substitution of one or more amino acids comprised into group 1 of mutations as discussed above in combination with a substitution of one or more amino acids comprised into group 2 of mutations. Without being bound to any theory, it has been verified by the inventors that aerolysin variants comprising one or more mutations comprised into group 1 of mutations may be further optimized in terms of functioning and/or activity if they further comprise also mutations comprised into group 2 of mutations, thereby providing mutated pores with improved or ameliorated features with regards to their ability to sense and/or characterise a target substrate.

In embodiments of the invention, a mutation in group 1 of mutations is coupled with a mutation in group 2 of mutations in a way that the mutated amino acids of both groups are sterically close one to the other. As a way of example, a mutation at position R282 (group 1 of mutations) in an aerolysin variant may be coupled with a mutation at position D216 (group 2 of mutations), and/or a mutation at position R220 (group 1 of mutations) in an aerolysin variant may be coupled with a mutation at position D222 (group 2 of mutations), and/or a mutation at position K238 (group 1 of mutations) in an aerolysin variant may be coupled with a mutation at position E258 (group 2 of mutations), and/or a mutation at position K242 (group 1 of mutations) in an aerolysin variant may be coupled with one or more mutations at positions K244, K246, E252, E254 (group 2 of mutations).

Further examples of suitable combinations of mutations according to the invention are the following:

K238A+D216A: K238A enhances the signal readout while D216A increase the capture capability for negatively charged target analytes such as DNA; K238A+R282A: K238A enhances the signal readout while R282A increase the capture capability for positively charged target analytes such as peptides;

In the frame of the invention, K238A could be replaced by K238Q or K242A, while D216A could be replaced by D216N or D222N or D222A; R282A could be replaced by R220A and R220W.

Accordingly, some suitable combinations according to the invention could be as follows:

For negatively charged molecular detection: K238A+D216A, K238Q+D216A, K242A+D216A; K238A+D216N, K238Q+D216N, K242A+D216N;

K238A+D222N, K238Q+D222N, K242A+D222N.

For positively charged molecular detection: K238A+R282A, K238Q+R282A, K242A+R282A; K238A+R220A, K238Q+R220A, K242A+R220A; K238A+R220W, K238Q+R220W, K242A+R220W; K244A+R282A, K246A+R282A, E252A+R282A, E254A+R282A; K244A+R220A, K246A+R220A, E252A+R220A, E254A+R220A; K244A+R220W, K246A+R220W, E252A+R220W, E254A+R220W.

The amino acids introduced into the variant may be naturally-occurring or non-naturally occurring derivatives thereof. The amino acids introduced into the variant may be D-amino acids.

The one or more modifications made to the identified region may concern the substitution of one or more amino acids in the region with amino acids present at the corresponding position(s) in homologues or paralogues of aerolysin. Four examples of homologues of aerolysin are shown in SEQ ID NOs: 2 to 7. The advantage of such substitutions is that they are likely to result in mutant monomers that form pores since the homologue monomers also form pores.

In addition to the specific mutations discussed above, the variant may include other mutations. These mutations do not necessarily enhance the ability of the monomer to interact with an analyte substrate such as a polynucleotide. The mutations may facilitate, for example, expression and/or purification. Over the entire length of the amino acid sequence of SEQ ID NO: 1, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 1 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example, the UWGCG Package provides the BESTFIT program which can be used to calculate homology, for example used on its default settings (Devereux et al (1984) Nucleic Acids Research 12, p387-395). The PILEUP and BLAST algorithms can be used to calculate homology or line up sequences (such as identifying equivalent residues or corresponding sequences (typically on their default settings)). Software for performing BLAST analyses is publicly available through the National Center for Biotechnology Information (http://www.ncbi.nlm.nih.gov/).

Amino acid substitutions may be made to the amino acid sequence of SEQ ID NO: 1 in addition to those discussed above, for example up to 1, 2, 3, 4, 5, 10, 20, 30 or even more substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 1 below. Where amino acids have similar polarity, this can also be determined by reference to the hydropathy scale for amino acid side chains in Table 2.

TABLE 1

| Chemical properties of amino acids | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |

TABLE 1-continued

Chemical properties of amino acids

| | | | |
|---|---|---|---|
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 2

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

The variant may comprise one or more substitutions outside of the region specified above in which amino acids are replaced with those at the corresponding position(s) in homologues and paralogues of aerolysin. Examples of homologues of aerolysin are shown in SEQ ID NOs: 2 to 7.

One or more amino acid residues of the amino acid sequence of SEQ ID NO: 1 may additionally be deleted from the variants described above. Up to 1, 2, 3, 4, 5, 10, 20 or 30 residues may be deleted, or more.

Variants may include fragments of SEQ ID NO: 1. Such fragments retain pore forming activity. This may be assayed as described above. Fragments may be at least 50, 100, 150, 200 or 250 amino acids in length. Such fragments may be used to produce the pores of the invention.

A fragment more preferably comprises the region from about position 216 to about position 282 of SEQ ID NO: 1 which is modified in accordance with the invention.

One or more amino acids may be alternatively or additionally added to the variants described above. An extension may be provided at the amino terminal or carboxy terminal of the amino acid sequence of the variant of SEQ ID NO: 1, including a fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

In addition to the modifications of the invention, a variant of SEQ ID NO: 1 may include one or more additional modifications, such as substitutions, additions or deletions. These modifications are preferably located in the stretches in the variant that correspond to from about position 1 to about position 206 and from about position 291 to about position 493 of SEQ ID NO: 1 (i.e. outside of the region modified in accordance with the invention).

The mutant monomers may be modified to assist their identification or purification, for example by the addition of histidine residues (a "his tag"), aspartic acid residues (an "asp tag"), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7): 497-505).

The mutant monomer may be labelled with a revealing label. The revealing label may be any suitable label which allows the pore to be detected. Suitable labels include, but are not limited to, fluorescent molecules, radioisotopes, enzymes, antibodies, antigens, polynucleotides, polyethylene glycols (PEGs), peptides and ligands such as biotin.

The mutant monomer may also be produced using D-amino acids. For instance, the mutant monomer may comprise a mixture of L-amino acids and D-amino acids. This is conventional in the art for producing such proteins or peptides.

The mutant monomer contains one or more specific modifications to facilitate interaction with a substrate, such as a polynucleotide, polypeptide or small molecule analyte. The mutant monomer may also contain other non-specific modifications as long as they do not interfere with pore formation. A number of non-specific side chain modifications are known in the art and may be made to the side chains of the mutant monomer.

Such modifications include, for example, reductive alkylation of amino acids by reaction with an aldehyde followed by reduction with NaBH4, amidination with methylacetimidate or acylation with acetic anhydride.

The mutant monomer can be produced using standard methods known in the art. The monomer may be made synthetically or by recombinant means. For example, the monomer may be synthesized by in vitro translation and transcription (IVTT). Suitable methods for producing pore monomers are discussed in International Applications WO 2010/004273, WO 2010/004265 or WO 2010/086603. Methods for inserting pores into membranes are discussed below.

A mutant monomer of the invention may be isolated, substantially isolated, purified or substantially purified. A mutant monomer of the invention is isolated or purified if it is completely free of any other components, such as lipids. A mutant monomer is substantially isolated if it is mixed with carriers or diluents which will not interfere with its intended use. For instance, a mutant monomer is substantially isolated or substantially purified if it is present in a form that comprises less than 10%, less than 5%, less than 2% or less than 1% of other components, such as lipids.

Polynucleotide sequences encoding a mutant monomer may be derived and replicated using standard methods in the art. Such sequences are discussed in more detail below. Polynucleotide sequences encoding a mutant monomer may be expressed in a bacterial host cell using standard techniques in the art. The mutant monomer may be produced in a cell by in situ expression of the polypeptide from a recombinant expression vector. The expression vector optionally carries an inducible promoter to control the expression of the polypeptide.

A mutant monomer may be produced in large scale following purification by e.g. any protein liquid chromatography system from pore producing organisms or after recombinant expression as described below. Typical protein liquid chromatography systems include FPLC, AKTA systems, the Bio-Cad system, the Bio-Rad BioLogic system and the Gilson FIPLC system.

In some embodiments, the mutant monomer is chemically modified. The mutant monomer can be chemically modified in any way and at any site. The mutant monomer is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. Suitable non-natural amino acids include, but are not limited to, 4-azido-L-phenylalanine (Faz).

The mutant monomer may be chemically modified by the attachment of any molecule. For instance, the mutant monomer may be chemically modified by attachment of a polyethylene glycol (PEG), a nucleic acid, such as DNA, a dye, a fluorophore or a chromophore. In some embodiments, the mutant monomer is chemically modified with a molecular adaptor that facilitates the interaction between a pore comprising the monomer and a target substrate analyte, particularly a target nucleotide or target polynucleotide. The presence of the adaptor improves the host-guest chemistry of the pore and the nucleotide or polynucleotide and thereby improves the sequencing ability of pores formed from the mutant monomer. The principles of host-guest chemistry are well-known in the art. The adaptor has an effect on the physical or chemical properties of the pore that improves its interaction with the nucleotide or polynucleotide. The adaptor may alter the charge of the barrel or channel of the pore or specifically interact with or bind to the nucleotide or polynucleotide thereby facilitating its interaction with the pore.

The molecular adaptor is preferably a cyclic molecule, for example a cyclodextrin, a species that is capable of hybridization, a DNA binder or interchelator, a peptide or peptide analogue, a synthetic polymer, an aromatic planar molecule, a small positively-charged molecule or a small molecule capable of hydrogen-bonding.

The adaptor may be cyclic. A cyclic adaptor preferably has the same symmetry as the pore. The adaptor typically interacts with the substrate analyte, nucleotide or polynucleotide via host-guest chemistry. The adaptor is typically capable of interacting with the nucleotide or polynucleotide. The adaptor comprises one or more chemical groups that are capable of interacting with the nucleotide or polynucleotide. The one or more chemical groups preferably interact with the nucleotide or polynucleotide by non-covalent interactions, such as hydrophobic interactions, hydrogen bonding, Van der Waal's forces, p-cation interactions and/or electrostatic forces.

Polynucleotide Binding Proteins

In certain embodiments, polynucleotide binding proteins may be covalently attached to the mutant monomer. The protein can be covalently attached to the pore using any method known in the art. The monomer and protein may be chemically fused or genetically fused. The monomer and protein are genetically fused if the whole construct is expressed from a single polynucleotide sequence. Genetic fusion of a pore to a polynucleotide binding protein is discussed in e.g. International Application WO 2010/004265.

If the polynucleotide binding protein is attached via cysteine linkage, the one or more cysteines have preferably been introduced to the mutant by substitution. Such substitutions are typically made in loop regions which have low conservation amongst homologues indicating that mutations or insertions may be tolerated. They are therefore suitable for attaching a polynucleotide binding protein. Such substitutions are typically made in residues 1 to 206 and 291 to 493 of SEQ ID NO: 1.

The polynucleotide binding protein may be attached directly to the mutant monomer or via one or more linkers. The polynucleotide binding protein may be attached to the mutant monomer using the hybridization linkers described e.g. in International Application WO 2010/086602. Alternatively, peptide linkers may be used. Peptide linkers are amino acid sequences. The length, flexibility and hydrophilicity of the peptide linker are typically designed such that it does not to disturb the functions of the monomer and molecule. Preferred flexible peptide linkers are stretches of 2 to 20, such as 4, 6, 8, 10 or 16 amino acids. More preferred flexible linkers include (SG)1, (SG)2, (SG)3, (SG)4 and the like, wherein S is serine and G is glycine. Preferred rigid linkers are stretches of 2 to 30, such as 4, 6, 8, 16 or 24, proline amino acids.

Making Mutant Aerolysin Monomers

The invention also provides a method of improving the ability of an aerolysin monomer comprising the sequence shown in SEQ ID NO: 1 to characterise an analyte such as a polynucleotide or peptide/polypeptide. The method comprises making one or more modifications within the region of from about position 207 to about position 290 of SEQ ID NO: 1 which alter the ability of the monomer to interact with an analyte and do not affect the ability of the monomer to form a pore. Preferred modifications include at least one modification at positions 220, 238, 242 and/or 282 of SEQ ID NO: 1. Other preferred modifications include at least one modification at positions 209, 216, 222, 244, 246, 252, 254 and 258 of SEQ ID NO: 1, with the proviso that said one or more amino acid substitution is not Q212R, R282G, N226Q, K238F, K238G, K238Y, K238C, T232K, Q212R, R282G, D209R, N226Q.

Any of the embodiments discussed above with reference to the mutant aerolysin monomers and below with reference to characterising polynucleotides/polypeptides equally apply to this method of the invention.

Constructs

The invention also provides a construct comprising two or more covalently attached monomers derived from aerolysin wherein at least one of the monomers is a mutant aerolysin monomer of the invention. The construct of the invention retains its ability to form a pore. One or more constructs of the invention may be used to form pores for characterising a target substrate.

One or more constructs of the invention may be used to form pores for characterising a target polynucleotide, such as sequencing a target polynucleotides. The construct may comprise 2, 3, 4, 5, 6, 7 or more monomers, most preferably 7 monomers. The two or more monomers may be the same or different. At least one monomer in the construct is a mutant monomer of the invention. The other monomers in the construct do not have to be mutant monomers of the invention. For instance, at least one monomer may comprise the sequence shown in SEQ ID NO: 1. At least one monomer in the construct may be a paralogue or homologue of SEQ ID NO: 1. Suitable homologues are shown in SEQ ID NOs: 2 to 7. Alternatively, at least one monomer may comprise the sequence shown in SEQ ID NO: 8. At least one monomer in the construct may be a paralogue or homologue of SEQ ID NO: 8. Suitable homologues are shown in SEQ ID NOs: 10 to 15.

Alternatively, at least one monomer may comprise a variant of SEQ ID NO: 1 which is at least 50% homologous to SEQ ID NO: 1 over its entire sequence based on amino acid identity, but does not include any of the specific mutations required by the mutant monomers of the invention. Alternatively, at least one monomer may comprise a variant of SEQ ID NO: 8 which is at least 50% homologous to SEQ ID NO: 8 over its entire sequence based on amino acid identity, but does not include any of the specific mutations required by the mutant monomers of the invention. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 1 or SEQ ID NO: 8 over the entire sequence. The variant may be a fragment or any other variant discussed above. Constructs of the invention may also comprise a variant of SEQ ID NO: 2 to 7 or SEQ ID NO: 10 to 15 which is at least 50% homologous or at least any of the other level of homology mentioned above to SEQ ID NO: 2 to 7 or SEQ ID NO: 10 to 15 over its entire sequence based on amino acid identity.

Any or all of the monomers in the construct may be a mutant monomer of the invention. The mutant monomers may be the same or different. In a more preferred embodiment, the construct comprises seven monomers and at least one of the monomers is a mutant monomer according to the invention.

The monomers may be genetically fused. Monomers are genetically fused if the whole construct is expressed from a single polynucleotide sequence. The coding sequences of the monomers may be combined in any way to form a single polynucleotide sequence encoding the construct. Genetic fusion is discussed e.g. in International Application WO 2010/004265.

The monomers may be genetically fused in any configuration. The monomers may be fused via their terminal amino acids. For instance, the amino terminus of the one monomer may be fused to the carboxy terminus of another monomer.

The two or more monomers may be genetically fused directly together. The monomers are preferably genetically fused using a linker. The linker may be designed to constrain or facilitate the mobility of the monomers. Preferred linkers are amino acid sequences (i.e. peptide linkers).

In another embodiment, the monomers are chemically fused. Monomers are chemically fused if they are chemically attached, for instance via a chemical crosslinker. Any of the chemical crosslinkers discussed above may be used. The linker may be attached to one or more cysteine residues or non-natural amino acids, such as Faz, introduced into a mutant monomer. Alternatively, the linker may be attached to a terminus of one of the monomers in the construct.

If a construct contains different monomers, crosslinkage of monomers to themselves may be prevented by keeping the concentration of linker in a vast excess of the monomers. Alternatively, a "lock and key" arrangement may be used in which two linkers are used. Only one end of each linker may react together to form a longer linker and the other ends of the linker each react with a different monomers. Such linkers are described for instance in International Application WO 2010/086602.

The invention also provides a method of producing a construct of the invention. The method comprises covalently attaching at least one mutant aerolysin monomer of the invention to one or more monomers derived from aerolysin. Any of the embodiments discussed above with reference to the construct of the invention equally apply to the methods of producing the constructs.

Polynucleotides

The present invention also provides polynucleotide sequences which encode a mutant monomer of the invention. The mutant monomer may be any of those discussed above. The polynucleotide sequence preferably comprises a sequence at least 50%, 60%, 70%, 80%, 90% or 95% homologous based on nucleotide identity to the sequence of SEQ ID NO: 9 over the entire sequence. There may be at least 80%, for example at least 85%, 90% or 95% nucleotide identity over a stretch of 600 or more contiguous nucleotides ("hard homology"). Homology may be calculated as described above. The polynucleotide sequence may comprise a sequence that differs from SEQ ID NO: 9 on the basis of the degeneracy of the genetic code.

The present invention also provides polynucleotide sequences which encode any of the genetically fused constructs of the invention, preferably two or more sequences encoding any of the genetically fused constructs of the invention or variants thereof as described above.

Polynucleotide sequences may be derived and replicated using standard methods in the art. Chromosomal DNA encoding wild-type aerolysin may be extracted from a pore producing organism, such as *Aeromonas hydrophila*. The gene encoding the pore monomer may be amplified using PCR involving specific primers. The amplified sequence may then undergo site-directed mutagenesis. Suitable methods of site-directed mutagenesis are known in the art and include, for example, combine chain reaction. Polynucleotides encoding a construct of the invention can be made using well-known techniques, such as those described in Sambrook, J. and Russell, D. (2001). Molecular Cloning: A Laboratory Manual, 3rd Edition. Cold Spring Harbor Laboratory Press, Cold Spring Harbor, NY The resulting polynucleotide sequence may then be incorporated into a recombinant replicable vector such as a cloning vector. The vector may be used to replicate the polynucleotide in a compatible host cell. Thus, polynucleotide sequences may be made by introducing a polynucleotide into a replicable vector, introducing the vector into a compatible host cell, and growing the host cell under conditions which bring about replication of the vector. The vector may be recovered from the host cell. Suitable host cells for cloning of polynucleotides are known in the art and described in more detail below.

The polynucleotide sequence may be cloned into suitable expression vector. In an expression vector, the polynucleotide sequence is typically operably linked to a control sequence which is capable of providing for the expression of the coding sequence by the host cell. Such expression vectors can be used to express a pore subunit.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different polynucleotide sequences may be introduced into the vector.

The expression vector may then be introduced into a suitable host cell. Thus, a mutant monomer or construct of the invention can be produced by inserting a polynucleotide sequence into an expression vector, introducing the vector into a compatible bacterial host cell, and growing the host cell under conditions which bring about expression of the polynucleotide sequence. The recombinantly-expressed monomer or construct may self-assemble into a pore in the host cell membrane. Alternatively, the recombinant pore produced in this manner may be removed from the host cell and e.g. inserted into another membrane. When producing pores comprising at least two different subunits, the different subunits may be expressed separately in different host cells as described above, removed from the host cells and assembled into a pore in a separate membrane.

The vectors may be for example plasmids, virus or phage vectors provided with an origin of replication, optionally a promoter for the expression of the said polynucleotide sequence and optionally a regulator of the promoter. The vectors may contain one or more selectable marker genes, for example a tetracycline resistance gene. Promoters and other expression regulation signals may be selected to be compatible with the host cell for which the expression vector is designed. A T7, trc, lac, ara or promoter is typically used.

The host cell typically expresses the pore subunit at a high level. Host cells transformed with a polynucleotide sequence will be chosen to be compatible with the expression vector used to transform the cell. The host cell is typically but not exclusively bacterial cells and preferably *Escherichia coli*. Host cells comprising an expression vector as described above are also contemplated in the present invention.

Pores

The invention also provides various pores. The pores of the invention are ideal for characterising substrate analytes. The pores of the invention are especially (but not exclusively) ideal for characterising, such as sequencing, polynucleotides because they might discriminate between different nucleotides with a high degree of sensitivity. The same is true, mutatis mutandis, for peptides and polypeptides. The pores can be used to characterise nucleic acids, such as DNA and RNA, including sequencing the nucleic acid and identifying single base changes. The pores of the invention could even distinguish between methylated and unmethylated nucleotides. The base resolution of pores of the invention is surprisingly high. The pores show almost complete separation of all four DNA nucleotides. The pores can be further used to discriminate between deoxycytidine monophosphate (dCMP) and methyl-dCMP based on the dwell time in the pore and the current flowing through the pore. Alternatively, the pores can be used to characterise polypeptides, including sequencing the amino acid sequence and identifying single amino acid changes.

The pores of the invention can also discriminate between different nucleotides under a range of conditions. In particular, the pores will discriminate between nucleotides under conditions that are favourable to the characterisation, such as sequencing, of polynucleotides. The extent to which the pores of the invention can discriminate between different nucleotides can be controlled by altering the applied potential, the salt concentration, the buffer, the temperature and/or the presence of additives, such as urea, betaine and DTT. This allows the function of the pores to be fine-tuned, particularly when sequencing. This is discussed in more detail below.

The pores of the invention may also be used to identify polynucleotide polymers from the interaction with one or more monomers rather than on a nucleotide by nucleotide basis. A pore of the invention may be isolated, substantially isolated, purified or substantially purified. A pore of the invention is isolated or purified if it is completely free of any other components, such as lipids or other pores. A pore is substantially isolated if it is mixed with carriers or diluents which will not interfere with its intended use. For instance, a pore is substantially isolated or substantially purified if it is present in a form that comprises less than 10%, less than 5%, less than 2% or less than 1% of other components, such as lipids or other pores. Alternatively, a pore of the invention may be present in a lipid bilayer.

A pore of the invention may be present as an individual or single pore. Alternatively, a pore of the invention may be present in a homologous or heterologous population or plurality of two or more pores.

Homo-Oligomeric Pores

The invention also provides a homo-oligomeric pore derived from aerolysin comprising identical mutant monomers of the invention. The monomers are identical in terms of their amino acid sequence. The homo-oligomeric pore of the invention is ideal for characterising, such as sequencing, polynucleotides. The homo-oligomeric pore of the invention may have any of the advantages discussed above.

The homo-oligomeric pore may contain any number of mutant monomers. The pore typically comprises two or more mutant monomers. One or more of the mutant monomers is preferably chemically modified as discussed above. In other words, one or more of the monomers being chemically modified (and the others not being chemically modified) does not prevent the pore from being homo-oligomeric as long as the amino acid sequence of each of the monomers is identical.

Hetero-Oligomeric Pores

The invention also provides a hetero-oligomeric pore derived from aerolysin comprising at least one mutant monomer of the invention, wherein at least one of the monomers differs from the others. The monomer differs from the others in terms of its amino acid sequence. The hetero-oligomeric pore of the invention is ideal for characterising, such as sequencing, polynucleotides or polypeptides. Hetero-oligomeric pores can be made using methods known in the art (e.g. Protein Sci. 2002 July; 11(7): 1813-24).

The hetero-oligomeric pore contains sufficient monomers to form the pore. The monomers may be of any type. The pore typically comprises seven monomers. The pore may comprise at least one monomer comprising the sequence shown in SEQ ID NO: 8, a paralogue thereof, a homologue thereof or a variant thereof, which does not necessarily have a mutation required by the mutant monomers of the invention. Suitable variants are any of those discussed above with reference to the constructs of the invention, including SEQ ID NOs: 8, 10, 11, 12, 13, 14, and 15 and variants thereof. In this embodiment, the remaining monomers are preferably mutant monomers of the invention.

In some embodiments, the pore comprises (a) one mutant monomer of the invention and (b) a sufficient number of identical monomers to form the pore, wherein the mutant monomer in (a) is different from the identical monomers in (b). The identical monomers in (b) preferably comprise the sequence shown in SEQ ID NO: 8, a paralogue thereof, a homologue thereof or a variant thereof which does not have a mutation required by the mutant monomers of the invention.

A hetero-oligomeric pore of the invention may comprises only one mutant aerolysin monomer of the invention. In another embodiment, all of the monomers in the hetero-oligomeric pore are mutant monomers of the invention and at least one of them differs from the others. In any of the embodiments discussed above, one or more of the mutant monomers may be chemically modified as discussed above. The presence of a chemical modification on one monomer does not result in the pore being hetero-oligomeric. The amino acid sequence of at least one monomer must differ from the sequence(s) of the other monomers. Methods for making pores are discussed in more detail below.

Construct-Containing Pores

The invention also provides a pore comprising at least one construct of the invention. A construct of the invention comprises two or more covalently attached monomers derived from aerolysin, wherein at least one of the monomers is a mutant aerolysin monomer of the invention. In other words, a construct must contain more than one monomer. At least two of the monomers in the pore are in the form of a construct of the invention. The monomers may be of any type.

A pore typically contains (a) one construct comprising two monomers and (b) a sufficient number of monomers to form the pore. The construct may be any of those discussed above. The monomers may be any of those discussed above, including mutant monomers of the invention. Another typical pore comprises more than one construct of the invention, such as two, three or four constructs of the invention. Such pores further comprise a sufficient number of monomers to form the pore. The monomer may be any of those discussed above.

Mutations can be introduced into the construct as described above. The mutations may be alternating, i.e. the mutations are different for each monomer within a two monomer construct and the constructs are assembled as a homo-oligomer resulting in alternating modifications. Alternatively, the mutations may be neighbouring, i.e. identical mutations are introduced into two monomers in a construct and this is then oligomerised with different mutant monomers. One or more of the monomers of the invention in a construct-containing pore may be chemically-modified as discussed above.

Producing Pores of the Invention

The invention also provides a method of producing a pore of the invention. The method comprises allowing at least one mutant monomer of the invention or at least one construct of the invention to oligomerise with a sufficient number of mutant aerolysin monomers of the invention, constructs of the invention or monomers derived from aerolysin to form a pore. If the method concerns making a homo-oligomeric pore of the invention, all of the monomers used in the method are mutant aerolysin monomers of the invention having the same amino acid sequence. If the method concerns making a hetero-oligomeric pore of the invention, at least one of the monomers is different from the others. Any of the embodiments discussed above with reference to the pores of the invention equally apply to the methods of producing the pores.

Methods of Sensing and/or Character/Sing Substrates

The invention provides a method of sensing and/or characterising a target substrate. The method comprises contacting the target substrate with a pore of the invention such that the target substrate moves through the pore. One or more characteristics of the target substrate are then measured as the substrate moves with respect to the pore using standard methods known in the art. One or more characteristics of the target substrate are preferably measured as the substrate moves through the pore. Steps (a) and (b) are preferably carried out with a potential applied across the pore. The applied potential may be a voltage potential. Alternatively, the applied potential may be a chemical potential. An example of this is using a salt gradient across an amphiphilic layer.

The method of the invention is for sensing and/or characterising a target substrate. The method is for sensing and/or characterising at least one substrate. The method may concern sensing and/or characterising two or more substrate.

The method may comprise sensing and/or characterising any number of substrate, such as 1, 2, 5, 10, 15, 20, 30, 40, 50, 100 or more substrate. The target substrate is preferably, but not limited to, a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant. The method may concern sensing and/or characterising two or more substrate of the same type, such as two or more proteins, two or more nucleotides or two or more pharmaceuticals. Alternatively, the method may concern sensing and/or characterising two or more substrate of different types, such as one or more proteins, one or more nucleotides and one or more pharmaceuticals.

The target substrate can be secreted from cells. Alternatively, the target substrate can be a substrate that is present inside cells such that the substrate must be extracted from the cells before the invention can be carried out.

In certain embodiments, the substrate is preferably an amino acid, a peptide, a polypeptide and/or a protein. The amino acid, peptide, polypeptide or protein can be naturally-occurring or non-naturally occurring.

The polypeptide or protein can include within them synthetic or modified amino acids. A number of different types of modification to amino acids are known in the art. Suitable amino acids and modifications thereof are above. For the purposes of the invention, it is to be understood that the target substrate can be modified by any method available in the art.

The protein can be for instance an enzyme, an antibody, a hormone, a growth factor or a growth regulatory protein, such as a cytokine. The cytokine may be selected from interleukins, preferably IFN-1, IL-1, IL-2, IL-4, IL-5, IL-6, IL-10, IL-12 and IL-13, interferons, and other cytokines. The protein may be a bacterial protein, a fungal protein, a virus protein or a parasite-derived protein.

In certain embodiments, the target substrate is preferably a nucleotide, an oligonucleotide or a polynucleotide. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide. Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (HDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate.

The nucleotides are preferably selected from AMP, TMP, GMP, UMP, dAMP, dTMP, dGMP or dCMP. The nucleotides may be abasic (i.e. lacking a nucleobase). The nucleotides may contain additional modifications. In particular, suitable modified nucleotides include, but are not limited to, 2'-amino pyrimidines (such as 2'-amino cytidine and 2'-amino uridine), 2'-hydroxyl purines (such as, 2'-fluoro pyrimidines (such as 2'-fluorocytidine and 2'-fluoro uridine), hydroxyl pyrimidines (such as 5'-a-P-borano uridine), 2'-O-methyl nucleotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

Oligonucleotides are short nucleotide polymers which typically have 50 or fewer nucleotides, such 40 or fewer, 30 or fewer, 20 or fewer, 10 or fewer or 5 or fewer nucleotides. The oligonucleotides may comprise any of the nucleotides discussed above, including the abasic and modified nucleotides.

The method of the invention is particularly suitable for sensing and/or characterising a target polynucleotide. A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. One or more nucleotides in the target polynucleotide may be modified, for instance with a label or a tag. Suitable labels are described above.

The nucleotides in the polynucleotide may be attached to each other in any manner. The nucleotides are typically attached by their sugar and phosphate groups as in nucleic acids. The nucleotides may be connected via their nucleobases as in pyrimidine dimers. The polynucleotide may be single stranded or double stranded. At least a portion of the polynucleotide is may be double stranded. A single stranded polynucleotide may have one or more primers hybridised thereto and hence comprise one or more short regions of double stranded polynucleotide. The primers may be the same type of polynucleotide as the target polynucleotide or may be a different type of polynucleotide.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The whole or only part of the target polynucleotide may be characterised using this method.

The target polynucleotide can be of any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target substrate, such as a target polynucleotide, is present in any suitable sample. The invention is typically carried out on a sample that is known to contain or suspected to contain the target substrate, such as the target polynucleotide. Alternatively, the invention may be carried out on a sample to confirm the identity of one or more target substrates, such as one or more target polynucleotides, whose presence in the sample is known or expected. Preferably, the sample is in a liquid form.

The sample may be a biological sample. The invention may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

The pore is typically present in a membrane. Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic molecules may be synthetic or naturally occurring.

The amphiphilic layer may be a monolayer or a bilayer. The amphiphilic layer is typically a planar lipid bilayer or a supported bilayer. The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome.

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials, organic and inorganic polymers such as polyamide, plastics such as Teflon® or elastomers such as two-component addition-cure silicone rubber, and glasses, and provides therefore the advantage of a manufacturing process free of any biologically-derived material. The solid state layer may be formed from monatomic layers, such as graphene, or layers that are only a few atoms thick.

Accordingly, one aspect of the invention relates to a system comprising a membrane having at least one pore according to the invention spanning across the membrane thickness. Preferably, the system comprises at least two chambers comprising a liquid medium, said chambers being separated by said membrane. The system according to the invention is particularly adapted and configured to act as a sensor or otherwise as analytical means for sensing and/or characterising a target substrate such as a small molecule, a polynucleotide or a polypeptide.

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. The method of the invention is typically carried out in vitro.

The substrate, such as a target polynucleotide, may be coupled to the membrane. This may be done using any known method. If the membrane is an amphiphilic layer, such as a lipid bilayer (as discussed in detail above), the substrate, such as a target polynucleotide, is preferably coupled to the membrane via a polypeptide present in the membrane or a hydrophobic anchor present in the membrane. The hydrophobic anchor is preferably a lipid, fatty acid, sterol, carbon nanotube or amino acid. The substrate, such as a target polynucleotide, may be coupled directly to the membrane. The substrate, such as a target polynucleotide, is preferably coupled to the membrane via a linker. Preferred linkers include, but are not limited to, polymers, such as polynucleotides, polyethylene glycols (PEGs) and polypeptides.

The substrate such as a target polynucleotide, may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used. In preferred embodiments, the substrate, such as a target polynucleotide, is coupled to an amphiphilic layer. Coupling of substrates, such as a target polynucleotide, to synthetic lipid bilayers has been carried out previously with various different tethering strategies.

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer.

Coupling of polynucleotides can also be achieved by a number of other means provided that a reactive group can be added to the polynucleotide. The addition of reactive groups to either end of DNA has been reported previously.

A selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labelling of synthetic oligonucleotide probes with terminal deoxynucleotidyl transferase." Anal Biochem 169 (2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5). Alternatively, either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends.

Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the target DNA amplified will contain a reactive group for coupling.

The pore used in the method of the invention is a pore of the invention (i.e. a pore comprising at least one mutant monomer of the invention or at least one construct of the invention). The pore may be chemically modified in any of the ways discussed above. The pore is preferably modified with a covalent adaptor that is capable of interacting with the target substrate as discussed above.

The method is preferably adapted for sensing and/or characterising a target polynucleotide and step (a) comprises contacting the target polynucleotide with the pore and possibly a polynucleotide binding protein so that the protein controls the movement of the target polynucleotide through the pore. The polynucleotide binding protein may be any protein that is capable of binding to the polynucleotide and controlling its movement through the pore.

The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the target sequence and controlling its movement through the pore.

There are two main strategies for sequencing polynucleotides using nanopores, namely strand sequencing and processing enzyme sequencing. The method of the invention may concern either strand sequencing or processing enzyme sequencing.

In strand sequencing, the DNA is translocated through the nanopore either with or against an applied potential. DNA polymerase that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner.

There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

In one embodiment, the method of sensing and/or characterising a target polynucleotide involves contacting the target sequence with a pore and a helicase enzyme. Any helicase may be used in the method. Helicases may work in two modes with respect to the pore. First, the method is preferably carried out using a helicase such that it controls movement of the target sequence through the pore with the field resulting from the applied voltage. In this mode the 5' end of the DNA is first captured in the pore, and the enzyme controls movement of the DNA into the pore such that the target sequence is passed through the pore with the field until it finally translocates through to the trans side of the bilayer.

Alternatively, the method is preferably carried out such that a helicase enzyme controls movement of the target sequence through the pore against the field resulting from the applied voltage. In this mode the 3' end of the DNA is first captured in the pore, and the enzyme controls movement of the DNA through the pore such that the target sequence is pulled out of the pore against the applied field until finally ejected back to the cis side of the bilayer.

In exonuclease sequencing, an exonuclease releases individual nucleotides from one end of the target polynucleotide and these individual nucleotides are identified as discussed below.

In another embodiment, the method of sensing and/or characterising a target polynucleotide involves contacting the target sequence with a pore and an exonuclease enzyme. Exonucleases are enzymes that typically latch onto one end of a polynucleotide and digest the sequence one nucleotide at a time from that end. The exonuclease can digest the polynucleotide in the 5' to 3' direction or 3' to 5' direction. The end of the polynucleotide to which the exonuclease binds is typically determined through the choice of enzyme used and/or using methods known in the art. Hydroxyl groups or cap structures at either end of the polynucleotide may typically be used to prevent or facilitate the binding of the exonuclease to a particular end of the polynucleotide.

The method involves contacting the polynucleotide with the exonuclease so that the nucleotides are digested from the end of the polynucleotide at a rate that allows characterization or identification of a proportion of nucleotides as discussed above.

The rate at which the exonuclease functions is typically slower than the optimal rate of a wild-type exonuclease. A suitable rate of activity of the exonuclease in the method of the invention involves digestion of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second.

The method of the invention involves in certain embodiments measuring one or more characteristics of the target substrate, such as a target polynucleotide. The method may involve measuring two, three, four or five or more characteristics of the target substrate, such as a target polynucleotide. For target polynucleotides, the one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured using the number of interactions between the target polynucleotide and the pore. For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below. For instance, methylcytosine may be distinguished from cytosine on the basis of the current flowing through the pore during its interaction with each nucleotide.

The invention also provides a method of estimating the sequence of a target polynucleotide. The invention further provides a method of sequencing a target polynucleotide. A variety of different types of measurements may be made. This includes without limitation: electrical measurements and optical measurements. Possible electrical measurements include: current measurements, impedance measurements, tunnelling measurements (Ivanov A P et al., Nano Lett. Jan. 12, 2011; 1l(I):279-85), and FET measurements (International Application WO 2005/124888). Optical measurements may be combined with electrical measurements (Soni G V et al., Rev Sci Instrum. 2010 January; 81(I):014301). The measurement may be a transmembrane current measurement such as measurement of ionic current flowing through a pore of the invention.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50): 17961-72, and International Application WO 2000/28312. Alternatively, electrical measurements may be made using a multi-channel system, for example as described in International Application WO 2009/077734 and International Application WO 2011/067559.

In a preferred embodiment, the method comprises:
(a) contacting the target polynucleotide with a pore of the invention and a polynucleotide binding protein such that the target polynucleotide moves through the pore and the binding protein controls the movement of the target polynucleotide through the pore; and
(b) measuring the current passing through the pore as the polynucleotide moves with respect to the pore wherein the current is indicative of one or more characteristics of the target polynucleotide and thereby characterising the target polynucleotide.

The methods may be carried out using any apparatus that is suitable for investigating a membrane/pore system in which a pore is inserted into a membrane. The method may be carried out using any apparatus that is suitable for transmembrane pore sensing. For example, the apparatus comprises a chamber comprising an aqueous solution and a barrier that separates the chamber into two sections. The barrier has an aperture in which the membrane containing the pore is formed. For instance, the methods may be carried out using the apparatus described in International Application WO 2008/102120.

The methods may involve measuring the current passing through the pore as the substrate, such as a target polynucleotide, moves with respect to the pore. Therefore, the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the substrate, such as a target polynucleotide, moves with respect to the pore. Suitable conditions for measuring ionic currents through transmembrane protein pores are known in the art. The method is typically carried out with a voltage applied across the membrane and pore. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), lithium chloride (LiCl), sodium chloride (NaCl) or caesium chloride (CsCl) is typically used. The salt concentration may be at saturation. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any suitable buffer may be used in the method of the invention. Typically, the buffer is HEPES. Another suitable buffer is Tris-HCl buffer. The methods are typically carried out at a pH of from 3.0 to 12.0, preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method is typically carried out in the presence of free nucleotides or free nucleotide analogues and an enzyme cofactor that facilitate the action of the polynucleotide binding protein, such as a helicase or an exonuclease. The free nucleotides may be one or more of any of the individual nucleotides discussed above. The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows a processing enzyme to function. The enzyme cofactor is preferably a divalent metal cation. The divalent metal cation is preferably Mg, Mn, Ca or Co. The enzyme cofactor is most preferably Mg2+.

The target polynucleotide may be contacted with the pore and the polynucleotide binding protein in any order. In is preferred that, when the target polynucleotide is contacted with the protein and the pore, the target polynucleotide firstly forms a complex with the protein. When the voltage is applied across the pore, the target polynucleotide/protein complex then forms a complex with the pore and controls the movement of the polynucleotide through the pore.

Methods of Identifying an Individual Nucleotide

The present invention also provides a method of sensing and/or characterising an individual nucleotide. In other words, the target substrate is an individual nucleotide. The method comprises contacting the nucleotide with a pore of the invention such that the nucleotide interacts with the pore and measuring the current passing through the pore during the interaction and thereby characterizing the nucleotide. The invention therefore involves nanopore sensing of an individual nucleotide.

Methods of Forming Sensors

The invention also provides a method of forming a sensor for sensing and/or characterising a target analyte such as a polynucleotide. In certain embodiments, the method comprises forming a complex between a pore of the invention and a polynucleotide binding protein, such as a helicase or an exonuclease. The complex may be formed by contacting the pore and the protein in the presence of the target analyte, such as a polynucleotide, and then applying a potential across the pore. The applied potential may be a chemical potential and/or a voltage potential as described above. Alternatively, the complex may be formed by covalently attaching the pore to the protein through methods known in the art.

The complex is a sensor for sensing and/or characterising the target analyte, such as a polynucleotide. The method preferably comprises forming a complex between a pore of the invention and a processing enzyme. Any of the embodiments discussed above equally apply to this method.

The invention also provides a sensor for sensing and/or characterising a target analyte such as a polynucleotide. The sensor comprises a complex between a pore of the invention and a polynucleotide binding protein. Any of the embodiments discussed above equally apply to the sensor of the invention.

Apparatus

The invention also provides an apparatus for sensing and/or characterising, such as sequencing, target analyte such as a polynucleotide in a sample. The apparatus may comprise (a) a plurality of pores of the invention and (b) a plurality of polynucleotide binding proteins, such as helicases or exonucleases. The apparatus may be any conventional apparatus for analyte analysis, such as an array or a chip.

The apparatus preferably comprises: a sensor device that is capable of supporting the plurality of pores and being operable to perform polynucleotide characterising or sequencing using the pores and proteins; at least one reservoir for holding material for performing the characterising or sequencing; a fluidics system configured to controllably supply material from the at least one reservoir to the sensor device; and a plurality of containers for receiving respective samples, the fluidics system being configured to supply the samples selectively from the containers to the sensor device.

EXAMPLES

Structural Characterization of Aerolysin Pore Mutants

According to a previous study, amino acids R282 and R220 at the cap region (pore entry), and K238 and K242 at the stem region (pore exit) are the two main sensing regions of the aerolysin pore, defined by distinctive steric (i.e., the main two constriction points located around R220 and K238) and electrostatic features (i.e., various layers of positively and negatively charged residues are present in these regions, see FIG. 1a). Steric hindrance and electrostatics are the two most important factors for molecular sensing in nanopore single-molecule approaches. To better understand the properties of these sensing regions, and how they modify the ability to sense different molecules, the inventors rationally designed several single-point mutants, and used molecular dynamics (MD) simulations to study their structural variation, ion selectivity and ionic conductance. In particular, to study the influence of the pore diameter, the amino acids at the sensing regions (R282, R220, K238 and K242) were replaced to alanine, as to enlarge the pore size (i.e., R282A, R220A, K238A, and K242A), or to tryptophan, for reducing the pore diameter (R282W, R220W, K238W, and K242W). Furthermore, to study the effect of electrostatics, the positively charged amino acid R220 was replaced to another positive (R220K), a negative (R220E), or a neutral (R220Q) amino acid with comparable side chain volume. Finally, analogous mutations were studied at the pore exit, i.e. K238R, K238N, K238E and K238Q, as illustrated in FIG. 1b.

Model systems for MD were then built. Briefly, the different pore mutants were prepared starting from an already equilibrated system comprising the aerolysin pore model embedded in a lipid bilayer, where single-point amino acid substitutions were introduced. After solvation in a 1 M KCl box and subsequent equilibration, all the systems were simulated for at least 200 ns of unrestrained MD applying a biased voltage of 150 mV. The pore model used in MD is a truncated version of the full length pore in which only the membrane spanning β-barrel is present without the extracellular membrane binding domains (FIG. 1a). Previous and current results showed that this minimal model is able to recapitulate the physico-chemical properties of the full-length pore, hinting at the β-barrel structure as the key structure determining translocation properties in aerolysin. It was then analyzed the diameter along the pore lumen for the various engineered proteins during MD simulations (FIG. 1c). As expected, replacements by alanine resulted in a wider diameter at the mutant position, and, in general, along the pore lumen. However, mutations at the pore exit (K238/K242) to alanine seemed to also affect the diameter at the pore entry, slightly decreasing it. Contrary to what was expected, replacements to tryptophan resulted in wider pores. This can be understood when comparing the side chain conformations along simulations. While the charged side chains of arginine and lysine residues extend completely to the lumen, interacting with water molecules and ions, the tryptophan residues turn back to the pore wall due to their partly hydrophobic nature. Interestingly, it was observed again a decrease in diameter at the pore entry for mutations to tryptophan in other positions along the pore. Overall, it seems that an increase in pore diameter at the pore exit creates a slight decrease in diameter at the pore entry. When it was analyzed the diameter at R220 and at K238 for all mutants (FIG. 1d), it was observed that mutations at K238 are predicted to actually affect the diameter of the first constriction point (R220), but the contrary is not true. Moreover, it was observed that R220 is the most rigid region in comparison to the rest of the pore, according to the calculation of root-mean-square fluctuations (RMSF) of the transmembrane inner barrel residues along the MD. Likely, this structural rigidity is linked to the higher stability of the double concentric β-barrel fold compared to the single β-barrel structure embedded in the lipid bilayer.

Figure 2:
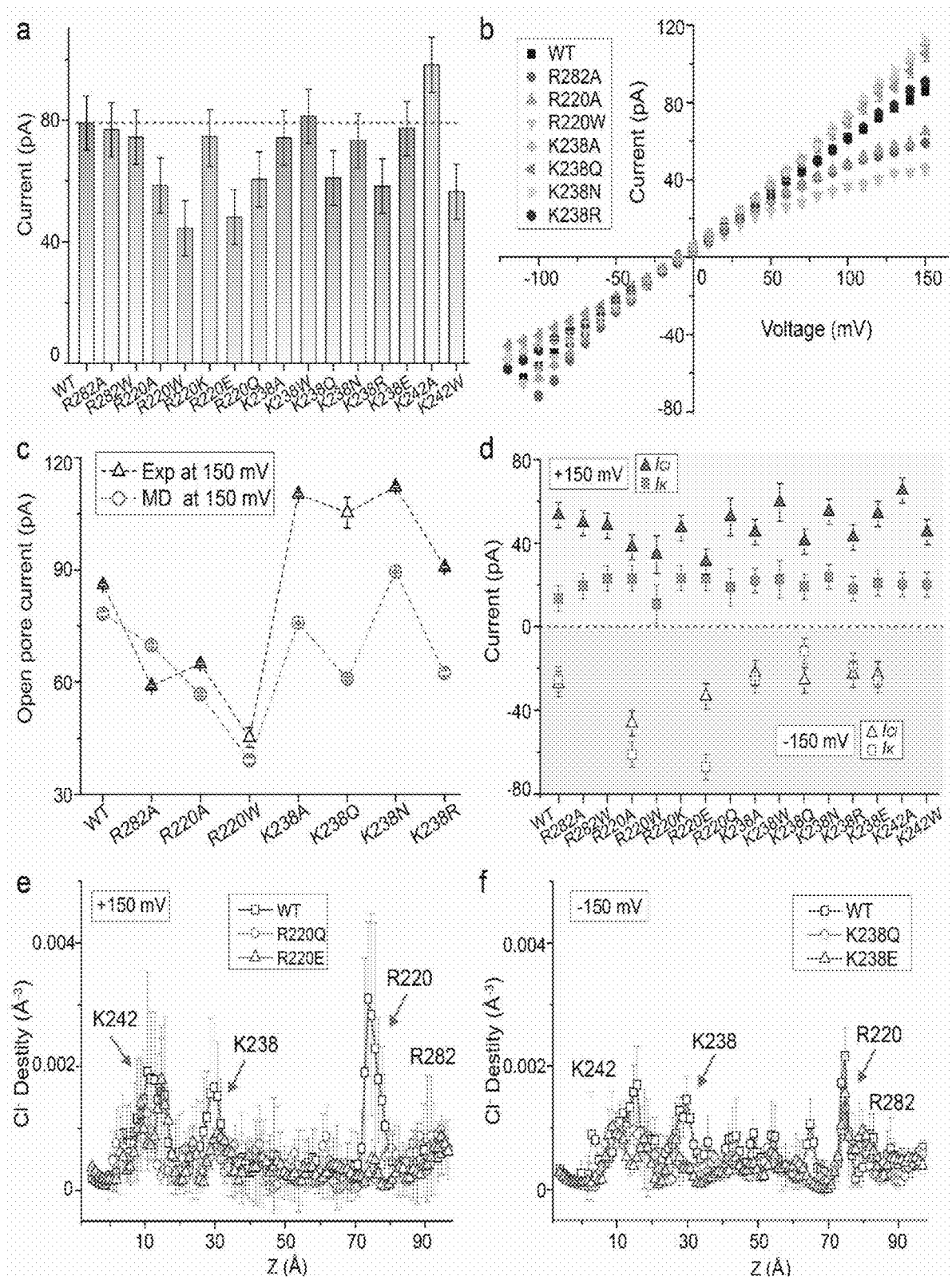

Characterization of Current Conductance and Ion Selectivity in Aerolysin Pore Mutants The open pore current of engineered pores at a fixed voltage (+150 mV) was calculated. A positive voltage implies translocation of negative ions from cis to trans chamber, while positive ions move from trans to cis (FIG. 1a). All current histograms are fitted with a Gaussian distribution and fitted values are shown in FIG. 2a. Surprisingly, larger pores did not always display a higher open pore current. For example, R220A, with pore diameter two times wider than wild-type (wt) at the main constriction region, was predicted to have a reduction of 27% in open pore current, indicating that ionic conductance does not depends merely on the pore size. The electrostatics at the pore lumen also plays an important role, and a decrease of the positive charge at the pore entry (R220A) could be responsible for this reduced ionic current, likely by failing to efficiently capture negative chloride ions.

Based on this analysis, the inventors selected relevant mutants for single-channel recording experiments: R282A, R220A and R220W to check the importance of positive residues at the cap region; K238A, K238Q, K238N, and K238R to gauge the influence of mutations at the pore exit. The details of pore production and single-channel recording experiments are reported in the methods section (see also FIG. 1a). The open pore current of the selected pores was measured at different voltages (FIG. 2b), showing results similar to those obtained by MD simulations (FIG. 2c). The removal of a positive amino acid at the cap domain (R220A and R282A) resulted in a decrease in current at positive voltages, and an increase at negative ones. For example, the open pore current of R220A (48.4±0.1 pA) decreased by 21% compared to the wt (61.5±0.7 pA) at 100 mV, while the amplitude of current at −100 mV (−62.3±0.1 pA) increased by 10% in comparison to the wt (−56.7±0.1 pA). This trend fits very well the MD predictions, therefore validating our models and the resulting molecular interpretations.

To further understand the nature of the current, it was calculated the current of $K^+$ ($I_K$) and of $Cl^-$ ($I_{Cl}$) ions, separately. As observed in FIG. 2d (blue area), the open pore current at +150 mV is mainly produced by $Cl^-$ ions for all mutants. Therefore, in principle, the replacement of positively charged amino acids at the pore entry with neutral residues will reduce $I_{Cl}$. As expected, R220A showed a 28% decrease in $I_{Cl}$ while $I_K$ was slightly increased compared to wt, which shows a good agreement with the 27% reduction in open pore current. The current calculations for wt, R220K, R220E, and R220Q further validated this hypothesis: the current of R220K (75.7±0.7 pA) is in fact similar to that of wt (78.2 pA±0.7), while the current in R220Q decreased by 24% (59.7±0.8 pA) and in R220E by 36% (50.0±0.3 pA). On the other hand, mutations at the stem region showed no obvious modification in potassium translocation under the positive voltages, suggesting that the cap region is the controller of ionic current. To better understand this observation, MD simulations were also carried out at a negative voltage, where potassium ions are now captured at the pore entry. As observed in FIG. 2d (red area), contrary to the positive voltage results, none of the ion species does dominate the total current for all engineered pores and wt. However, the R220A and R220E showed a clear increase of $I_K$. This is explained by an increase in potassium uptake at the cap region, when compared to its stem uptake at positive potentials. Therefore, FIG. 2d highlights a behavior that has not been observed in other nanochannels, e.g. α-Hemolisin (α-HL), that is, the total current is mostly controlled by the electrostatics at the cap region, which allows capturing either negative or positive ions depending on the applied voltage.

To better understand these differences in ion uptake and selectivity along the pore, it was computed the averaged density of $Cl^-$ and $K^+$ in wt and mutants both under positive and negative voltages. The volume inside the channel was discretized along the pore axis, and the average was taken over all trajectories originated from the wt structure. As illustrated in FIG. 2e, the $Cl^-$ density in wt and R220Q/E mutants was calculated under a positive voltage (150 mV). The replacement of the positively charged amino acid in wt (arginine) to neutral (glutamine, R220Q) or negative (glutamic acid, R220E) residues dramatically reduced the density of $Cl^-$ at the mutated site. The reduction of $Cl^-$ density along the pore suggests, again, a reduction of $Cl^-$ uptake at the cap in the pore entry mutants. A similar effect was observed, as expected, for $Cl^-$ density in K238Q/E mutants at a negative voltage (FIG. 2f). Interestingly, it was observed that the overall density of $Cl^-$ is reduced at this negative voltage when compared to the positive one, suggesting again the chloride capture is larger at the cap region than the stem. In addition, a strong increase in potassium selectivity for neutral mutants (R220Q and K238Q), and for negative ones (R220E and K238E), was observed.

Furthermore, the influence of side chain size was studied by the same calculations for R220A and R220Q: no difference in $Cl^-$ density were observed, suggesting that the side chain volume did not significantly influence ion selectivity. Therefore, while the cap region is mainly responsible for ion uptake, ion selectivity in aerolysin is predicted to be mostly controlled by electrostatics, while pore size may have a minor role.

Single Stranded DNA Sensing is Modulated by K238 Mutations

Figure 3:
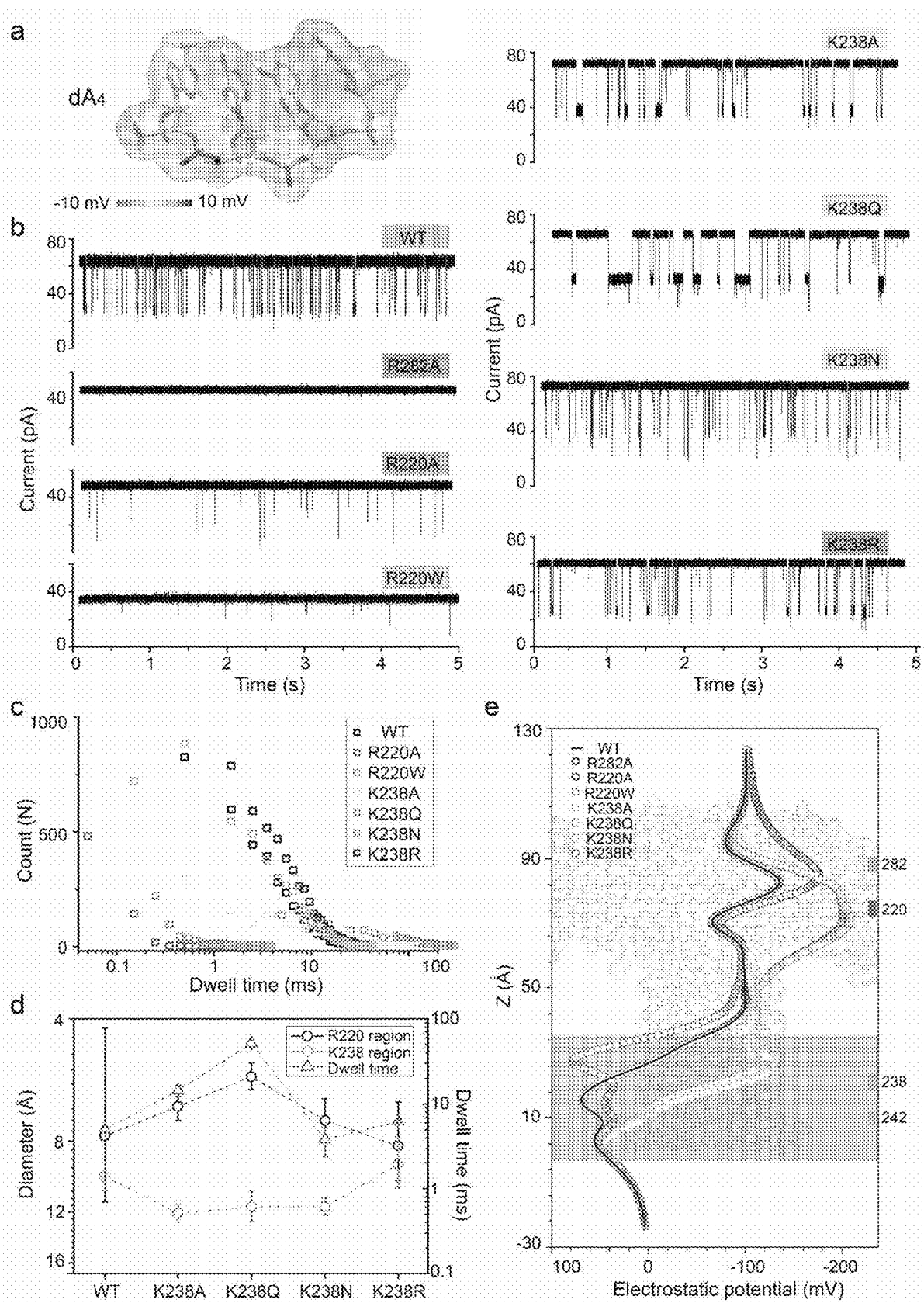

To test the sensing abilities of these engineered pores, translocation experiments was first performed for single-stranded DNA (ssDNA). The ssDNA used here is composed of 4 adenines, i.e., $dA_4$. As illustrated in FIG. 3a, $dA_4$ was added into the cis chamber after a single pore formed in a lipid bilayer, and then the translocation events were collected at various voltages ranging from +80 mV to +160 mV (raw current traces at +100 mV are reported in FIG. 3b). In comparison to wt, no signal was obtained for the R282A pores and very few events for R220A and R220W, revealing that the positively charged amino acids located at the cap region are crucial for capturing negatively charged molecules, such as ssDNA (FIG. 3c).

The dwell time distribution for thousands of $dA_4$ events was fitted by a falling exponential function (FIG. 3c) and the fitted values are reported in FIG. 3d (red triangles). For mutations at the R220 position (R220A and R220W), the dwell time of events is really short (0.12±0.02 ms and 0.15±0.03 ms, respectively). Additionally, the dwell time of these two mutants remained unvaried under different applied voltages, demonstrating that the ssDNA did not translocate the R220A and R220W pores. In order to better understand this observation, the electrostatic potential along the pore for wt and mutants was calculated under the same applied voltage of +100 mV, using the GCMC/BD Ion Simulator (FIG. 3e). The R282A mutation reverses the potential at this point, resulting in a force working in the opposite direction and repelling the negatively charged DNA. This explains why there is barely any signal observed for the R282A variant. However, these data suggest that R282A mutants may work well for capturing positively charged molecules (see below). Additionally, we could also observe that mutations at the R220 region did not vary as much the potential at the pore entry, allowing DNA molecules to be captured but impairing efficient ssDNA crossing.

Figure 6:
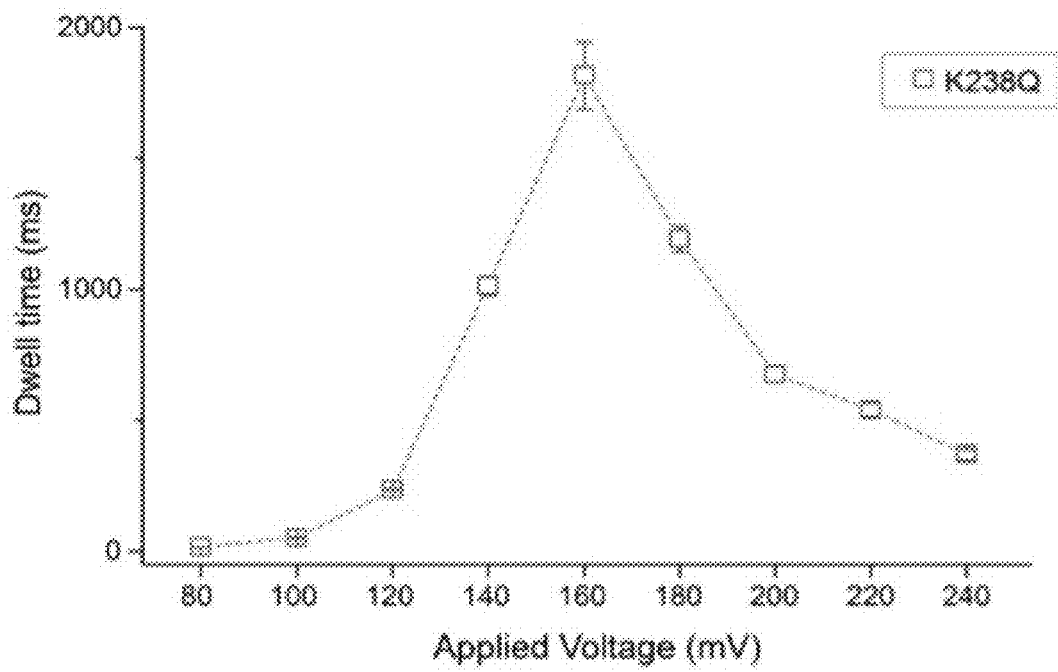
FIG. 6 shows the dwell time of dA4 upon addition into the K238Q pore.

For mutations at the K238 position, the frequency of events did not change a lot except for K238Q but the dwell time of $dA_4$ was largely affected in all mutations (FIGS. 3b and c). The frequency f was calculated as $f=1/T_{on}$, where $T_{on}$ is the inter-event interval for peptide crossing determined by single exponential fitting. Moreover, the dwell times experienced an exponential decrease at higher applied voltages, proving that $dA_4$ is actually translocated in these mutant pores. Notably, K238Q presents a unique property that allows $dA_4$ to translocate when the applied voltages are higher than +160 mV (FIG. 6). The three mutants, K238A, K238Q and K238N, remove a positively charged amino acid at the pore exit, and therefore possess a similar variation in electrostatic profile when compared to wt (FIG. 3e). Therefore, the dwell time variation induced by mutations at the K238 region are not easily explained by electrostatic arguments and could have a purely steric explanation. When it was compared the diameter size at the K238 region with the obtained dwell time of $dA_4$ translocation in different mutants (blue circles in FIG. 3d), no correlation was obtained. Then, considering that the chloride capturing at the cap side is the most important factor of ionic current, and that mutations at the pore exit modify diameter at the pore entry according to previous results (FIG. 1d), it was studied the diameter at the R220 region (black circles in FIG. 3d) and observed a correlation with dwell time. For example, K238Q constricted the diameter of R220 region to 5.6±0.5 Å and therefore slowed the $dA_4$ translocation from 1.4±2.1 ms to 1815.0±127.5 ms (at +160 mV), which means the translocation speed of $dA_4$ through the K238Q pore is around 453 ms per base, more than 1000 times slower than wt pores. Furthermore, it was observed an obvious reduction in the width of $I_{res}/I_0$ distributions ($I_{res}$ is the mean current blockade, while $I_0$ is the open pore current) for K238Q, demonstrating that having access to longer dwell times permits to evaluate the blockade current more accurately. Therefore, by making mutations at the stem region, it is possible to obtain significant modifications of the translocation properties at the cap region, allowing for a fine tuning of the molecular sensing properties.

Peptide Sensing by Engineered Aerolysin Nanopores

Figure 4:
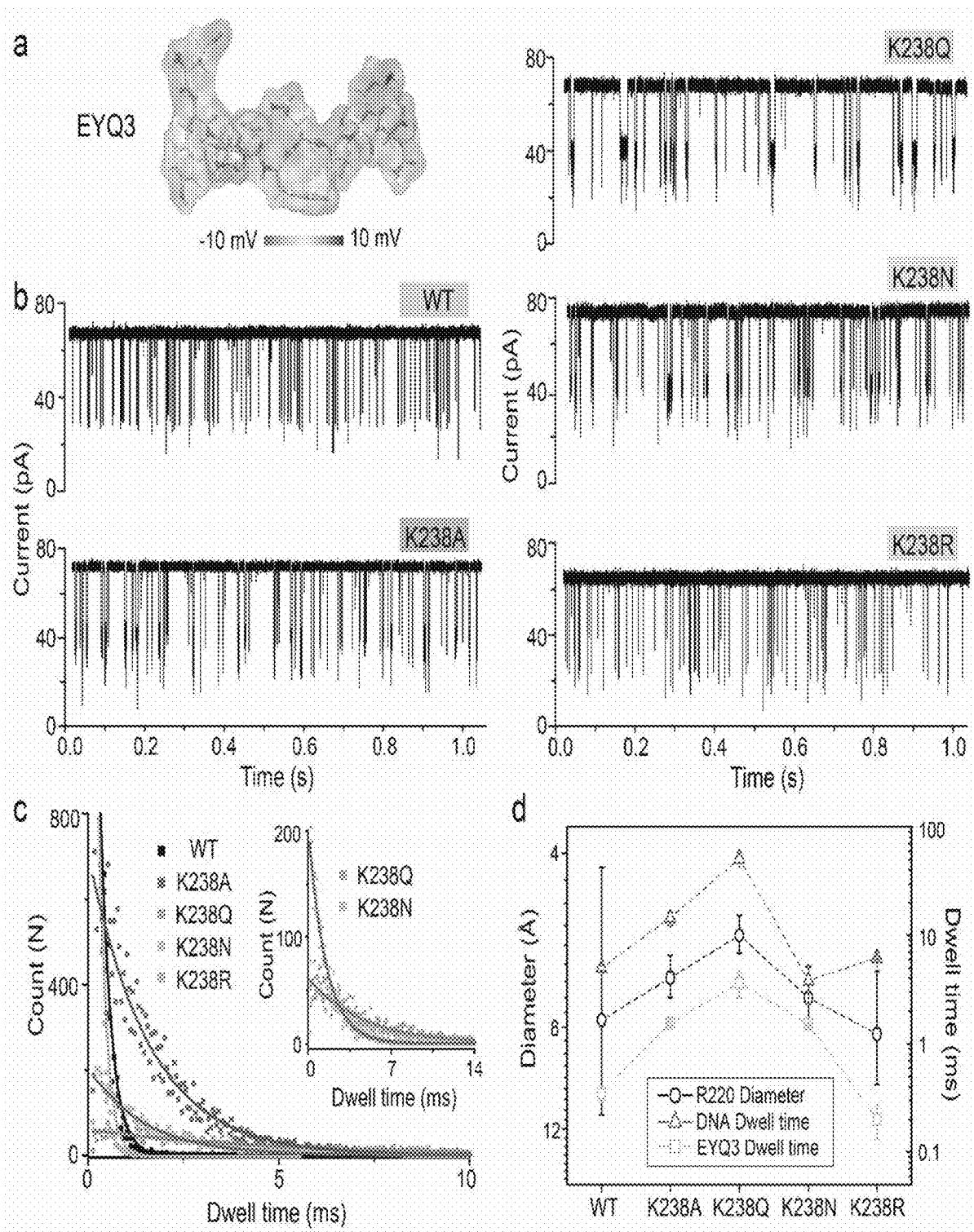

With the aim to extend the application of these pore mutants to a wider range of sensing tasks, it was then measured their capabilities during peptides translocation. It was first tested a negatively charged peptide, with sequence EYQEYQEYQ, named EYQ3 (FIG. 4a), which by design is expected to present similar translocation properties as ssDNA. Under a positive voltage (100 mV), K238A, K238Q and K238N mutants showed significantly prolonged dwell time with respect to wt pores (FIG. 4b), as it was observed for $dA_4$ translocation. The fitted values are 1.6±0.1 ms, 3.6±0.2 ms, 1.5±0.1 ms, and 0.4±0.1 ms, respectively (FIG. 4c). K238R mutants on the other hand have a behavior (0.2±0.2 ms) similar to the wt pores. As for $dA_4$ experiments, the EYQ3 dwell time correlates well with the diameter at the R220 region (FIG. 4d), while the frequency of events remained constantly except for K238Q. Therefore, the results show how directed mutations at the K238 region can be used to modulate the molecular sensing properties of aerolysin nanopores for the negatively charged molecules in general, including both DNA and peptides. Notably, the dwell time of EYQ3 across the wt and mutant pores is almost 10 times faster than that of $dA_4$ (FIG. 4d). In this context, having discovered mutations (e.g., K238Q) that can significantly affect the translocation time by one order of magnitude has potential for developing aerolysin as a general single-molecule sensing device.

Figure 5:
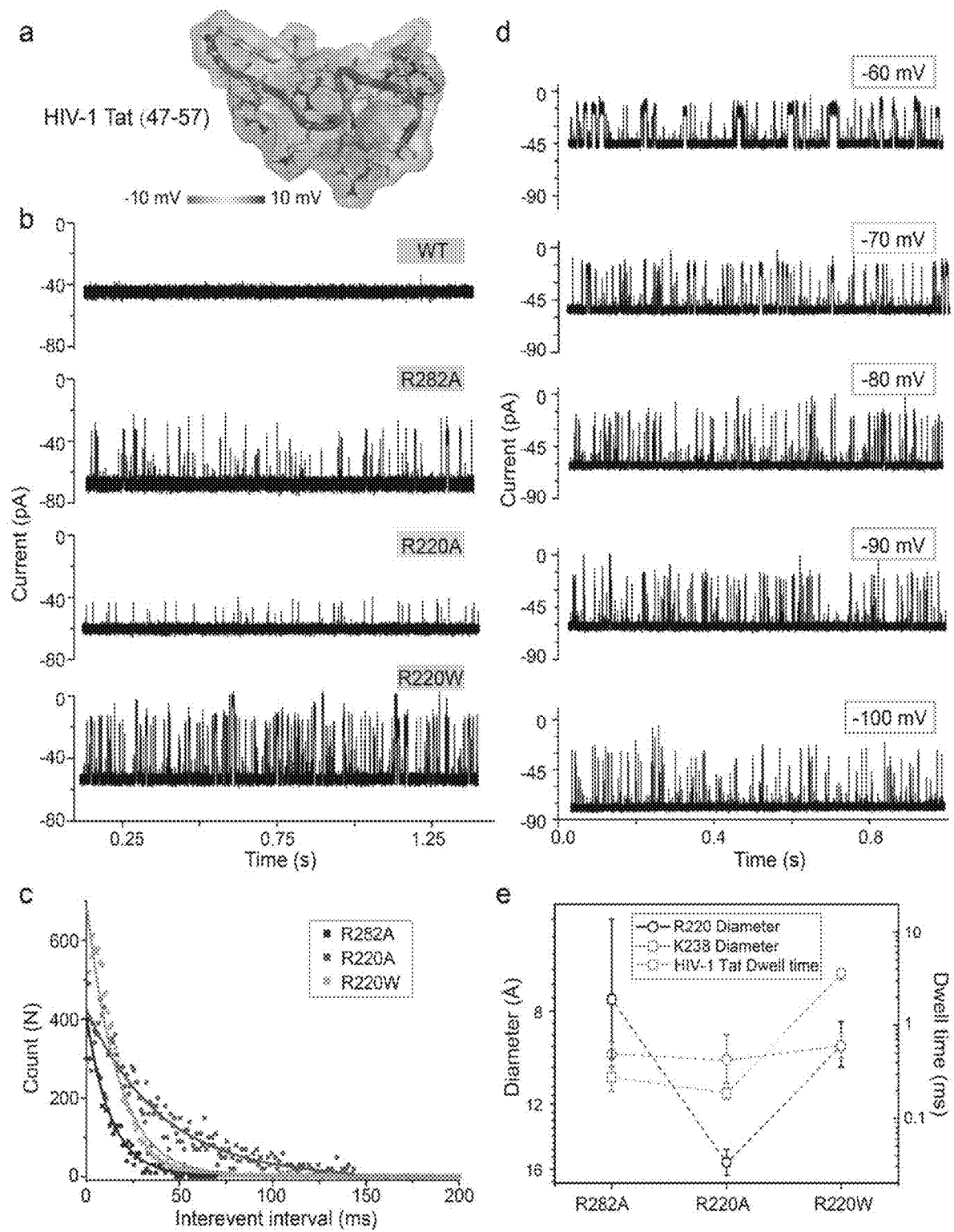
Figure 7:
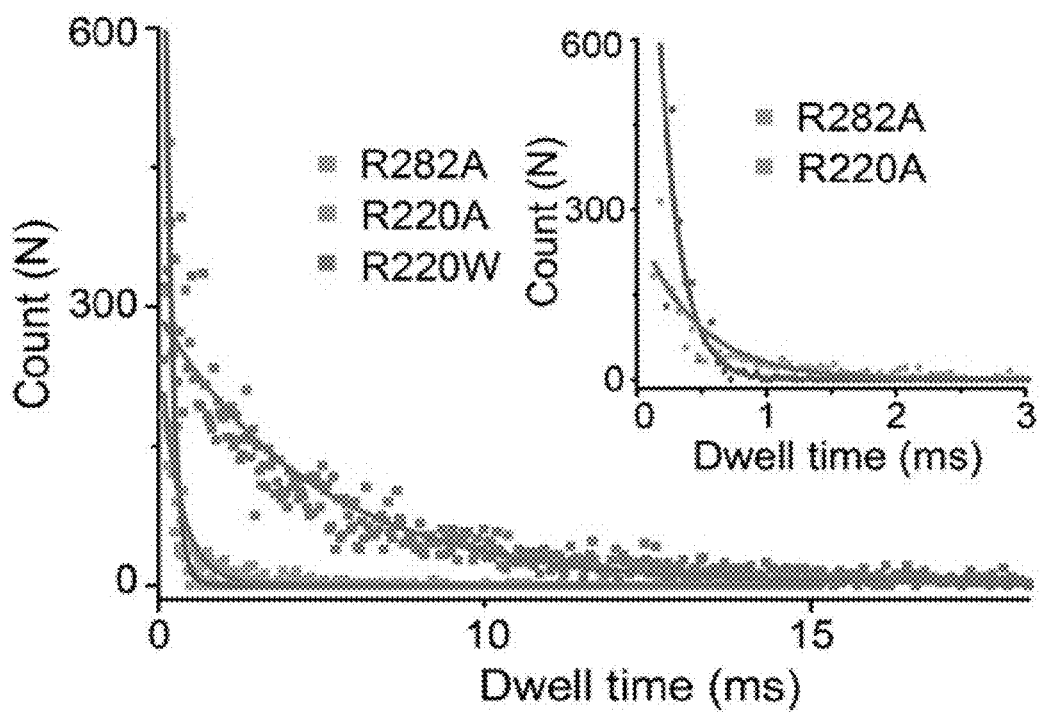
FIG. 7 shows the dwell time distributions of HIV-1 Tat (47-57) through the R282A (light grey), R220A (grey) and R220W (dark grey) mutant pores, respectively. The values were determined by the single exponential fitting.

Next, the translocation of polycationic peptides was studied, using a short segment (47-57) of the HIV-1 Tat protein (FIG. 5a), with sequence YGRKKRRQRRR, which is highly basic and hydrophilic. Considering its features, HIV-1 Tat (47-57) was added into the c/s side of the chamber and applied a negative voltage (100 mV) to drive it into the nanopore. For the wt pores, barely any signal was obtained, suggesting that aerolysin has a poor capability to capture highly positive peptides, which can be rationalized by the positive electrostatic potential at the mouth of the. In a previous study of α-HL, K131 D7, a mutant with a negatively charged ring at the trans entrance was able to capture the polycationic nanocarriers. Here it was shown that, as the positively charged amino acids in the cap region were replaced by the neutral amino acids, they are able to capture polycationic peptides. As shown in FIG. 5b, R282A, R220A and R220W mutants exhibited an excellent capture ability for this polycationic peptide. The event frequencies of R282A, R220A and R220W are 74.3±5.2 $s^{-1}$, 24.5±1.8 $s^{-1}$ and 59.4±0.5 $s^{-1}$, respectively (FIG. 5c, dwell times for HIV-1 Tat (47-57) are shown in FIG. 7). To confirm that the signal is caused by actual translocation events of HIV-1 Tat (47-57) rather than transient bumping/interaction at the pore entry, a range of applied voltages from −60 mV to −100 mV was explored (FIG. 5d). It is visually clear how the dwell time decreases as the amplitude of applied voltages increases, demonstrating that the signals are caused by the translocations of peptides. When compared the dwell time of HIV-1 Tat (47-57) with the diameter of the R220 and K238 region (FIG. 5e), it seems to fit the diameter at the first constriction point better. Therefore, these results show that engineered aerolysin nanopores can be also extended for sensing molecules that are prevalently positively charged, so as the HIV-1 Tat (47-57) peptide. Molecules with different chemical signature could in principle be specifically detected by using appropriate mutant pores. Such possibility makes the development of aerolysin-based nanopores very promising for single-molecule proteomic approaches.

Aerolysin differs from other biological nanopores mainly by its pore length, which is ~10 nm in comparison to the length of α-HL (~8.5 nm) and MspA (~8.0 nm). This longer length could be in principle a drawback for developing high sensitivity and has likely led to a lack of attention for aerolysin as a molecular sensor. Based on structural and functional knowledge of this pore, this unique feature seems more likely an advantage rather than a drawback. First, the longer pore together with the narrower diameter of aerolysin allows a slower translocation as to sense molecules without the need of an external support (e.g. additional DNA immobilization, adapter incorporation, or the processing enzyme), which is a common challenge to all nanopore sequencing approaches. Second, this long pore may allow for broader and finer modifications in order to tune sensing of diverse molecules. Therefore, unraveling the structure-function relationship of aerolysin appears as a promising and powerful way to develop nanopores with desirable features. Herein, a large set of mutants was rationally designed and studied by fully integrating in silico and in vitro experiments. Using this strategy, the inventors managed to get novel insights into the translocation mechanism of aerolysin and was able to select a set of pore mutants highly promising for DNA and peptide sensing.

More important are however the molecular sensing properties, which are mainly related to the diameter of the narrowest pore section. The cap region is responsible for determining which molecule will be captured, acting therefore as a selectivity filter. Thus, it was possible to modify aerolysin properties as to natively capture under applied voltage not only negative, but also positive molecules, being R220W the most promising mutant for this task. On the other hand, the second constriction region (K238) was observed to be responsible for modulating molecule translocation time. This analysis was herein extended to a broader set of mutants and, more importantly, it was possible to determine the mechanism of this regulation.

In spite of modifying the molecular translocation by modifications of size or electrostatics at the mutant region, mutations at the stem are able to influence the diameter at the cap, which is related to the differences in observed dwell time. Therefore, the first constriction point is not only a selectivity filter, but also a sensitivity spot, and mutations at other regions along the pore (mainly K238) allow tuning its diameter for controlling the dwell time of different molecules. In particular the K238Q mutant, which produces a smaller diameter at R220 and increases the dwell time, could be used for sensing molecules which translocate faster than DNA, e.g. negative peptides.

In summary, the factors altering the open pore current, ion selectivity and structure variation of engineered aerolysin-based nanopores have been systematically studied and explained at the molecular level combining microscopic observations done in silico with macroscopic measurements in vitro. Altogether, it was proved that the sensitive diameter of aerolysin can be precisely controlled from 5 Å to 15 Å by site-direct mutagenesis, significantly extending the spectrum of detection capabilities for aerolysin nanopores. The ion selectivity can be tuned by the replacement of charged amino acids both at the double β-barrel cap domain, and at the stem pore exit region, providing a basic control of selectivity for specific biomolecules (i.e., ssDNA, and negatively and positively charged peptides). Finally, the strong correlation observed between the diameter at the pore cap region and the dwell time of mutants establishes the unique double β-barrel domain of aerolysin pores as the most important structural motif for molecular sensing, opening more precise rational avenues for tuning aerolysin sensing capabilities.

METHODS

Molecular Modeling and Simulations

The aerolysin pore was modeled using a previously prepared equilibrated system comprising an aerolysin pore model embedded in a lipid bilayer, where single-point amino acid substitutions were introduced. The pore structure in the initial system comprised the membrane spanning ·-barrel (i.e., the membrane binding domains were not considered in the simulations), which remained stable for all MD simulations like the complete pore unit. The membrane bilayer was modeled by 1-Palmitoyl-2-oleoylphosphatidylcholine (POPC) lipids using the CHARMM-gui server.

The mutant pores embedded in the equilibrated membrane were afterwards solvated on an 11×11×15.0 nm 1M KCl water box. After minimization using the steepest descent algorithm (integration step of 1 fs and 1000 kJ mol$^{-1}$ nm$^{-1}$ of maximum force), the solvent box was equilibrated for 0.1 ns (integration step of 2 fs), using position restraints for the protein and lipids (i.e., 10 kcal mol$^{-1}$ Å$^{-2}$ for protein backbone heavy atoms, 5 kcal mol$^{-1}$ Å$^{-2}$ for protein side chain heavy atoms, and 2.5 kcal mol$^{-1}$ Å$^{-2}$ for restraining the lipid tail and lipid head groups close to the membrane surface). All MD simulations were run using the GROMACS software (version 4.8), with the CHARMM36 force field, the SHAKE algorithm on all the bonds involving hydrogen atoms, and Particle-Mesh Ewald, treating the electrostatic interactions with periodic boundary conditions. We chose an integration step of 2 fs. A temperature of 22° C. was controlled with the Nose-Hoover thermostat and the Parrinello-Rahman method was used for semi-isotropic pressure coupling. Biased voltage were applied with the z-dimension kept fixed, and with no need for using further position restraints. The backbone root-mean-square deviation (RMSD) along the simulations shows a fast equilibration of all mutants within the first 10 ns of simulation. All systems were simulated for at least 200 ns.

The diameter of the pore along the MD simulations was calculated using the PoreWalker software, taking into consideration only the last 150 ns of the trajectories and selecting a frame every 10 ns, using a window size of 3 Å for the calculation. The electrostatic potential was calculated using the GCMC/BD Ion Simulator, with an applied 100 mV voltage and using an implicit membrane model of 4 nm thickness. As input, we used for each pore mutant the full-length conformation, while the relative truncated versions of the pore mutants were used in MD simulations. Although using slightly different models and conditions, both calculations provided a consistent description of the electrostatic potential inside the pore barrel. Once oriented with respect to the membrane plane using the PPM server, the pore coincides to the membrane position observed during MD simulations. The GCMC/BD Ion simulator considers the solvent and lipids implicitly. The electrostatic surface was calculated by using the PBEQ software, using the same protein conformations as for the GCMC/BD Ion simulator, and following the parameters described in Cao C. et al. (Nature Communications volume 9, Article number: 2823, 2018). For ion density, calculations were performed on the last 150 ns, where all mutants reached equilibration. All trajectory frames were fitted to the starting wt pore structure. Calculation of density for water, Cl$^-$ and K$^+$ was performed with VMD plugin volmap density, using a resolution of 1 Å, a step of 100 ps, and averaged as to obtain mean and standard deviation. The radius of the pore cavity occupied by water and average density of Cl$^-$ and K$^+$ inside the cavity was then calculated. The location of the pore axis was determined by the center of mass of the protein, then the volume was sliced into layers of 1 Å and the radius was found by the iterative process: first, the radius was assigned to be 1 Å and then it was increased by 0.5 Å while the ratio of water/non-water atoms inside the added ring was larger than 25%.

Expression and Purification of Recombinant Aerolysin Mutants

The aerolysin full length sequence was cloned in the pET22b vector with a C-terminal hexa-histidine tag to aid purification. The QuikChange II XL kit from Agilent Technologies was used for performing site-directed mutagenesis on the aerolysin gene, following manufacturer's instructions. Recombinant proteins were expressed and purified from BL21 DE3 pLys *E. coli* cells. Cells were grown to an optical density of 0.6-0.7 in Luria-Bertani (LB) media. Protein expression was induced by the addition of 1 mM isopropyl β-D-1-thiogalactopyranoside (IPTG) and subsequent growth over night at 20° C. Cell pellets were resuspended in lysis buffer (20 mM Sodium phosphate pH 7.4, 500 mM NaCl) mixed with cOmplete™ Protease Inhibitor Cocktail (Roche) and then lysed by sonication. The resulting suspensions were centrifuged (12.000 rpm for 35 min at 4° C.) and the supernatants were applied to an HisTrap HP column (GE Healthcare) previously equilibrated with lysis buffer. The proteins were eluted with a gradient over 40 column volumes of elution buffer (20 mM Sodium phosphate pH 7.4, 500 mM NaCl, 500 mM Imidazole), and buffer exchanged into final buffer (20 mM Tris, pH 7.4, 500 mM NaCl) using a HiPrep Desalting column (GE Healthcare). The purified proteins were flash frozen in liquid nitrogen and stored at −20° C.

Single-Channel Recording Experiments

Phospholipid of 1,2-Diphytanoyl-sn-glycero-3-phosphocholine powder (Avanti Polar Lipids, Inc., Alabaster, AL, USA) was dissolved in decane (Sigma-Aldrich Chemie GmbH, Buchs, Switzerland) for a final concentration of 1.0 mg per 50 μl. Purified protein was diluted to the concentration of 0.2 μg/ml and then incubated with Trypsin-EDTA (Sigma-Aldrich Chemie GmbH, Buchs, S G Switzerland) for 1 h at room temperature. Phospholipid membranes were formed across a Delrin bilayer cup (Warner Instruments, Hamden, CT, USA), which separated the chamber into two part, cis and trans. After added aerolysin protein into the cis chamber, it could self-assemble to form a heptameric pore in the membrane. The electrolyte used here is 1.0 M KCl solution buffered with 10 mM Tris and 1.0 mM EDTA, titrated to pH=7.4. Two matched Ag/AgCl electrodes were used to record the ionic currents. Then, the current traces were amplified and measured with a patch clamp amplifier (Axon 200B) equipped with a Digidata 1440A/D converter (Molecular Devices, Sunnyvale, CA, USA). The signals were filtered at 5 kHz and acquired with Clampex 10.4 software (Molecular Devices, Sunnyvale, CA, USA) at a sampling rate of 100 kHz. The data were analysed using Clampfit and OriginLab 8.0 (OriginLab Corporation, Northampton, MA, USA) software.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

```
SEQUENCE LISTING
>sp|P09167|AERA_AERHY Aerolysin OS = Aeromonas hydrophila
GN = aerA
                                                           SEQ ID NO: 1
AEPVYPDQLRLFSLGQGVCGDKYRPVNREEAQSVKSNIVGMMGQWQIS

GLANGWVIMGPGYNGEIKPGTASNTWCYPTNPVTGEIPTLSALDIPDGD

EVDVQWRLVHDSANFIKPTSYLAHYLGYAWVGGNHSQYVGEDMDVTR

DGDGWVIRGNNDGGCDGYRCGDKTAIKVSNFAYNLDPDSFKHGDVTQ

SDRQLVKTVVGWAVNDSDTPQSGYDVTLRYDTATNWSKTNTYGLSEKV

TTKNKFKWPLVGETELSIEIAANQSWASQNGGSTTTSLSQSVRPTVPAR

SKIPVKIELYKADISYPYEFKADVSYDLTLSGFLRWGGNAWYTHPDNRPN

WNHTFVIGPYKDKASSIRYQWDKRYIPGEVKWWDWNWTIQQNGLSTM

QNNLARVLRPVRAGITGDFSAESQFAGNIEIGAPVPLAADSKVRRARSVD

GAGQGLRLEIPLDAQELSGLGFNNVSLSVTPAANQ

>sp|Q06306|AER5_AERHY Aerolysin-5 OS = Aeromonas hydrophila
GN = ahh5
                                                           SEQ ID NO: 2
AEPVYPDQLRLFSLGQEVCGDKYRPITREEAQSVKSNIVNMMGQWQIS

GLANGWVIMGPVYNGEIKPGSASNTWCYPVNPVTGEIPTLSALDIPDGD

EVDVQWRLVHDSANFIKPTSYLAHYLGYAWVGGNHSQYVGEDMDVTR

DGDGWVIRGNNDGGCEGYRCGEKTAIKVSNFAYNLDPDSFKHGDVTQS

DRQLVKTVVGWAINDSYTPQSAYDVTLRYDTATNWSKTNTYGLSEKVTT

KNKFKWPLVGETELSIEIAANQSWASQNGGSTTTSLSQSVRPTVPARSKI

PVKIELYKADISYPYEFKADVSYDLTLSGFLRWGGNAWYTHPDNRPNWN

HTFVIGPYKDKASSIRYQWDKRYIPGEVKWWDWNWTIQQNGLSTMQNN

LARVLRPVRAGITGDFSAESQFAGNIEIGAPVPLAADGKAPRALSARRGE

QGLRLAIPLECRKSSPGLASATSA

>sp|Q06304|AERA_AERSO Aerolysin OS = Aeromonas sobria
GN = asa1
                                                           SEQ ID NO: 3
AEPVYPDQVKWAGLGTGVCASGYRPLTRDEAMSIKGNLVSRMGQWQIT

GLADRWVIMGPGYNGEIKQGTAGETWCYPNSPVSGEIPTLSDWNIPAG

DEVDVQWRLVHDNDYFIKPVSYLAHYLGYAWVGGNHSPYVGEDMDVT

RVGDGWLIKGNNDGGCSGYRCGEKSSIKVSNFSYTLEPDSFSHGQVTE

SGKQLVKTITANATNYTDLPQQVVVTLKYDKATNWSKTDTYSLSEKVTTK
```

NKFQWPLVGETELAIEIAASQSWASQKGGSTTETVSVEARPTVPPHSSL

PVRVALYKSNISYPYEFKAEVNYDLTMKGFLRWGGNAWYTHPDNRPTW

EHTLLLGPFRGQGEQHPLPVDKRYIPGEVKWWDWNWTISEYGLSTMQN

NLGRVLRPIRSAVTGDFYAESQFAGDIEIGQPQTRSAKAAQLRSASAEEV

ALTSVDLDSEALANEGFGNVSLTIVPVQ

>sp|Q06305|AER3_AERHY Aerolysin-3 OS = *Aeromonas hydrophila*
GN = ahh3
SEQ ID NO: 4

AEPVYPDQLRLFSLGQEVCGDKYRPVNREEAQSVKSNIVGMMGQWQIS

GLANGWVIMGPGYNGEIKPGSASSTWCYPTNPATGEIPTLSALDIPDGD

EVDVQWRLVHDSANFIKPTSYLAHYLGYAWVGGNHSQYVGEDMDVTR

DGDGWVIRGNNDGGCDGYRCGDKTSIKVSNFAYNLDPDSFKHGDVTQ

SDRQLVKTVVGWAINDSDTPQSGYDVTLRYDTATNWSKTNTYGLSEKV

TTKNKFKWPLVGETELSIEIAANQSWASQNGGSPTTSLSQSVRPTVPAH

SKIPVKIELYKADISYPYEFKADVSYDLTLSGFLRWGGNAWYTHPDNRPN

WNHTFVIGPYKDKASSIRYQWDKRYIPGEVKWWDWNWTIQQNGLPTM

QNNLAKVLRPVRAGITGDFSAESQFAGNIEIGAPVPAAASHSSRARNLS

AGQGLRLEIPLDAQELSGLGFNNVSLSVTPAANQ

>sp|P09166|AERA_AEREN Aerolysin OS = *Aeromonas enteropelogenes*
GN = aerA
SEQ ID NO: 5

NAAEPIYPDQLRLFSLGEDVCGTDYRPINREEAQSVRNNIVAMMGQWQI

SGLANNWVILGPGYNGEIKPGKASTTWCYPTRPATAEIPVLPAFNIPDGD

AVDVQWRMVHDSANFIKPVSYLAHYLGYAWVGGDHSQFVGDDMDVIQ

EGDDWVLRGNDGGKCDGYRCNEKSSIRVSNFAYTLDPGSFSHGDVTQ

SERTLVHTVVGWATNISDTPQSGYDVTLNYTTMSNWSKTNTYGLSEKVS

TKNKFKWPLVGETEVSIEIAANQSWASQNGGAVTTALSQSVRPVVPARS

RVPVKIELYKANISYPYEFKADMSYDLTFNGFLRWGGNAWHTHPEDRPT

LSHTFAIGPFKDKASSIRYQWDKRYLPGEMKWWDWNWAIQQNGLATM

QDSLARVLRPVRASITGDFRAESQFAGNIEIGTPVPLGSDSKVRRTRSVD

GANTGLKLDIPLDAQELAELGFENVTLSVTPARN

>sp|Q08676|AERA_AERSA Aerolysin OS = *Aeromonas salmonicida*
GN = ash3
SEQ ID NO: 6

WHEPVYPDQVKWAGLGTGVCASGYRPLTRDEAMSIKGNLVSRMGQW

QITGLADRWVIMGPGYNGEIKQGTAGETWCYPNSPVSGEIPTLSDWNIP

AGDEVDVQWRLVHDNDYFIKPVSYLAHYLGYAWVGGNHSPYVGEDMD

VTRVGDGWLIKGNNDGGCSGYRCGEKSSIKVSNFSYTLEPDSFSHGQV

TESGKQLVKTITANATNYTDLPQQVVVTLKYDKATNWSKTDTYSLSEKVT

TKNKFQWPLVGETELAIEIAASQSWASQKGGSTTETVSVEARPTVPPHS

SLPVRVALYKSNISYPYEFKAEVNYDLTMKGFLRWGGNAWYTHPDNRP

TWEHTFRLGPFRGQGEQHPLPVDKRYIPGEVKWWDWNWTISEYGLST

MQNNLGRVLRPIRSAVTGDFYAESQFAGDIEIGQPQTRSAKAAQLRSAS

AEEVALTSVDLDSEALANEGFGNVSLTIVPVQ

```
>sp|Q06303|AER4_AERHY Aerolysin-4 OS = Aeromonas hydrophila
GN = ahh4
                                                        SEQ ID NO: 7
AEPVYPDQLRLFSLGQEVCGDKYRPVNREEAQSIKSNIVGMMGQWQIS

GLANGWVIMGPGYNGEIKPGSASSTWCYPTNPATGEIPTLSALDIPDGD

EVDVQWRLVHDSANFIKPTSYLAHYLGYAWVGGNHSQYVGEDMDVTR

DGDGWVIRGNNDGGCDGYRCGDKTSIKVSNFAYNLDPDSFKHGDVTQ

SDRQLVKTVVGWAINDSDTPQSGYDVTLRYDTATNWSKTNTYGLSEKV

TTKNKFKWPLVGETELSIEIAANQSWASQNGGSTTTSLSQSVRPTVPAH

SKIPVKIELYKADISYPYEFKADVSYDLTLSGFLRWGGNAWYTHPDNRPN

WNHTFVIGPYKDKASSIRYQWDKRYIPGEVKWWDWNWTIQQNGLPTM

QNNLAKVLRPVRAGITGDFSAESQFAGNIEIGAPVPVAAASHSSRARNLS

AGQGLRLEIPLDAQELSGLGFNNVSLSVTPAANQ

>sp|P09167|AERA_AERHY Aerolysin OS = Aeromonas hydrophila
GN = aerA without C-terminal propeptide
                                                        SEQ ID NO: 8
AEPVYPDQLRLFSLGQGVCGDKYRPVNREEAQSVKSNIVGMMGQWQIS

GLANGWVIMGPGYNGEIKPGTASNTWCYPTNPVTGEIPTLSALDIPDGD

EVDVQWRLVHDSANFIKPTSYLAHYLGYAWVGGNHSQYVGEDMDVTR

DGDGWVIRGNNDGGCDGYRCGDKTAIKVSNFAYNLDPDSFKHGDVTQ

SDRQLVKTVVGWAVNDSDTPQSGYDVTLRYDTATNWSKTNTYGLSEKV

TTKNKFKWPLVGETELSIEIAANQSWASQNGGSTTTSLSQSVRPTVPAR

SKIPVKIELYKADISYPYEFKADVSYDLTLSGFLRWGGNAWYTHPDNRPN

WNHTFVIGPYKDKASSIRYQWDKRYIPGEVKWWDWNWTIQQNGLSTM

QNNLARVLRPVRAGITGDFSAESQFAGNIEIGAPVPL

>cds for P09167|AERA_AERHY Aerolysin OS = Aeromonas hydrophila
GN = aerA (including C-terminal peptide)
                                                        SEQ ID NO: 9
gcagagcccg tctatccaga ccagcttcgc ttgttttcat tgggccaagg ggtctgtggc gacaagtatc gccccgtcaa tcgagaagaa gcccaaagcg ttaaaagcaa tattgtcggc atgatgggc  aatggcaaat aagcgggctg ccaacggct  gggtcattat ggggccgggt tataacggtg aaataaaacc agggacagcg tccaatacct ggtgttatcc gaccaatcct gttaccggtg aaataccgac actgtctgcc ctggatattc cagatggtga cgaagtcgat gtgcagtggc gactggtaca tgacagtgcg aatttcatca aaccaaccag ctatctggcc cattacctcg gttatgcctg ggtgggcggc aatcacagcc aatatgtcgg cgaagacatg gatgtgaccc gtgatggcga cggctgggtg atccgtggca acaatgacgg cggctgtgac ggctatcgct gtggtgacaa gacggccatc aaggtcagca acttcgccta aacctggat cccgacagct tcaagcatgg cgatgtcacc cagtccgacc gccagctggt caagactgtg gtgggctggg cggtcaacga cagcgacacc ccccaatccg gctatgacgt caccctgcgc tacgacacag ccaccaactg gtccaagacc aacacctatg gcctgagcga aaggtgacc accaagaaca agttcaagtg gccactggtg ggggaaaccc aactctccat cgagattcgt gccaatcagt cctgggcgtc ccagaacggg ggctcgacca ccacctccct gtctcagtcc gtgcgaccga ctgtgccggc ccgctccaag atcccggtga agatagagct ctacaaggcc gacatctcct atccctatga gttcaaggcc gatgtcagct atgacctgac cctgagcggc ttcctgcgct ggggcggcaa cgcctggtat acccacccgg acaaccgtcc gaactggaac
```

```
cacaccttcg tcataggtcc gtacaaggac aaggcgagca gcattcgcta ccagtgggac aagcgttaca tcccgggtga agtgaagtgg tgggactgga actggaccat acagcagaac ggtctgtcta ccatgcagaa caacctggcc agagtgctgc gcccggtgcg ggcggggatc accggtgatt tcagtgccga gagccagttt gccggcaaca tagagatcgg tgctcccgtg ccgctcgcgg ctgacagcaa ggtgcgtcgt gctcgcagtg tggacggcgc tggtcaaggc ctgaggctgg agatcccgct cgatcgcgaa gagctctccg gcttggctt caacaagtca gcctcagcgt ga
```

\>sp|Q06306|AER5_AERHY Aerolysin-5 OS = *Aeromonas hydrophila*
GN = ahh5 without C-terminal propeptide
SEQ ID NO: 10

AEPVYPDQLRLFSLGQEVCGDKYRPITREEAQSVKSNIVNMMGQWQIS

GLANGWVIMGPVYNGEIKPGSASNTWCYPVNPVTGEIPTLSALDIPDGD

EVDVQWRLVHDSANFIKPTSYLAHYLGYAWVGGNHSQYVGEDMDVTR

DGDGWVIRGNNDGGCEGYRCGEKTAIKVSNFAYNLDPDSFKHGDVTQS

DRQLVKTVVGWAINDSYTPQSAYDVTLRYDTATNWSKTNTYGLSEKVTT

KNKFKWPLVGETELSIEIAANQSWASQNGGSTTTSLSQSVRPTVPARSKI

PVKIELYKADISYPYEFKADVSYDLTLSGFLRWGGNAWYTHPDNRPNWN

HTFVIGPYKDKASSIRYQWDKRYIPGEVKWWDWNWTIQQNGLSTMQNN

LARVLRPVRAGITGDFSAESQFAGNIEIGAPVPL

\>sp|Q06304|AERA_AERSO Aerolysin OS = *Aeromonas sobria*
GN = asa1 without C-terminal propeptide
SEQ ID NO: 11

AEPVYPDQVKWAGLGTGVCASGYRPLTRDEAMSIKGNLVSRMGQWQIT

GLADRWVIMGPGYNGEIKQGTAGETWCYPNSPVSGEIPTLSDWNIPAG

DEVDVQWRLVHDNDYFIKPVSYLAHYLGYAWVGGNHSPYVGEDMDVT

RVGDGWLIKGNNDGGCSGYRCGEKSSIKVSNFSYTLEPDSFSHGQVTE

SGKQLVKTITANATNYTDLPQQVVVTLKYDKATNWSKTDTYSLSEKVTTK

NKFQWPLVGETELAIEIAASQSWASQKGGSTTETVSVEARPTVPPHSSL

PVRVALYKSNISYPYEFKAEVNYDLTMKGFLRWGGNAWYTHPDNRPTW

EHTLLLGPFRGQGEQHPLPVDKRYIPGEVKWWDWNWTISEYGLSTMQN

NLGRVLRPIRSAVTGDFYAESQFAGDIEIGQPQ

\>sp|Q06305|AER3_AERHY Aerolysin-3 OS = *Aeromonas hydrophila*
GN = ahh3 without C-terminal propeptide
SEQ ID NO: 12

AEPVYPDQLRLFSLGQEVCGDKYRPVNREEAQSVKSNIVGMMGQWQIS

GLANGWVIMGPGYNGEIKPGSASSTWCYPTNPATGEIPTLSALDIPDGD

EVDVQWRLVHDSANFIKPTSYLAHYLGYAWVGGNHSQYVGEDMDVTR

DGDGWVIRGNNDGGCDGYRCGDKTSIKVSNFAYNLDPDSFKHGDVTQ

SDRQLVKTVVGWAINDSDTPQSGYDVTLRYDTATNWSKTNTYGLSEKV

TTKNKFKWPLVGETELSIEIAANQSWASQNGGSPTTSLSQSVRPTVPAH

SKIPVKIELYKADISYPYEFKADVSYDLTLSGFLRWGGNAWYTHPDNRPN

WNHTFVIGPYKDKASSIRYQWDKRYIPGEVKWWDWNWTIQQNGLPTM

QNNLAKVLRPVRAGITGDFSAESQFAGNIEIGAPVPV

>sp|P09166|AERA_AEREN Aerolysin OS = *Aeromonas enteropelogenes*
GN = aerA without C-terminal propeptide
SEQ ID NO: 13

NAAEPIYPDQLRLFSLGEDVCGTDYRPINREEAQSVRNNIVAMMGQWQI

SGLANNWVILGPGYNGEIKPGKASTTWCYPTRPATAEIPVLPAFNIPDGD

AVDVQWRMVHDSANFIKPVSYLAHYLGYAWVGGDHSQFVGDDMDVIQ

EGDDWVLRGNDGGKCDGYRCNEKSSIRVSNFAYTLDPGSFSHGDVTQ

SERTLVHTVVGWATNISDTPQSGYDVTLNYTTMSNWSKTNTYGLSEKVS

TKNKFKWPLVGETEVSIEIAANQSWASQNGGAVTTALSQSVRPVVPARS

RVPVKIELYKANISYPYEFKADMSYDLTFNGFLRWGGNAWHTHPEDRPT

LSHTFAIGPFKDKASSIRYQWDKRYLPGEMKWWDWNWAIQQNGLATM

QDSLARVLRPVRASITGDFRAESQFAGNIEIGTPVPL

>sp|Q08676|AERA_AERSA Aerolysin OS = *Aeromonas salmonicida*
GN = ash3 without C-terminal propeptide
SEQ ID NO: 14

WHEPVYPDQVKWAGLGTGVCASGYRPLTRDEAMSIKGNLVSRMGQW

QITGLADRWVIMGPGYNGEIKQGTAGETWCYPNSPVSGEIPTLSDWNIP

AGDEVDVQWRLVHDNDYFIKPVSYLAHYLGYAWVGGNHSPYVGEDMD

VTRVGDGWLIKGNNDGGCSGYRCGEKSSIKVSNFSYTLEPDSFSHGQV

TESGKQLVKTITANATNYTDLPQQVVVTLKYDKATNWSKTDTYSLSEKVT

TKNKFQWPLVGETELAIEIAASQSWASQKGGSTTETVSVEARPTVPPHS

SLPVRVALYKSNISYPYEFKAEVNYDLTMKGFLRWGGNAWYTHPDNRP

TWEHTFRLGPFRGQGEQHPLPVDKRYIPGEVKWWDWNWTISEYGLST

MQNNLGRVLRPIRSAVTGDFYAESQFAGDIEIGQPQ

>sp|Q06303|AER4_AERHY Aerolysin-4 OS = *Aeromonas hydrophila*
GN = ahh4 without C-terminal propeptide
SEQ ID NO: 15

AEPVYPDQLRLFSLGQEVCGDKYRPVNREEAQSIKSNIVGMMGQWQIS

GLANGWVIMGPGYNGEIKPGSASSTWCYPTNPATGEIPTLSALDIPDGD

EVDVQWRLVHDSANFIKPTSYLAHYLGYAWVGGNHSQYVGEDMDVTR

DGDGWVIRGNNDGGCDGYRCGDKTSIKVSNFAYNLDPDSFKHGDVTQ

SDRQLVKTVVGWAINDSDTPQSGYDVTLRYDTATNWSKTNTYGLSEKV

TTKNKFKWPLVGETELSIEIAANQSWASQNGGSTTTSLSQSVRPTVPAH

SKIPVKIELYKADISYPYEFKADVSYDLTLSGFLRWGGNAWYTHPDNRPN

WNHTFVIGPYKDKASSIRYQWDKRYIPGEVKWWDWNWTIQQNGLPTM

QNNLAKVLRPVRAGITGDFSAESQFAGNIEIGAPVPV

---

The invention claimed is:

1. A mutant aerolysin pore comprising at least one variant polypeptide of SEQ ID NO: 8 having one or more amino acid substitutions at one or more positions corresponding to positions 220, 238, 242, 282, 209, 216, 222, 244, 246, 252, 254 and 258 with the proviso that said one or more amino acid substitutions are not Q212R, R282G, N226Q, K238F, K238G, K238Y, K238C, T232K, Q212R, R282G, D209R, N226Q.

2. A method of sensing and/or characterising a target substrate comprising:

(a) contacting the target substrate with the mutant aerolysin pore of claim 1 so to allow the movement of the target substrate through said pore and a portion of the target substrate interacts with said pore; and (b) measuring a current passing through said pore, thereby sensing and/or characterising the target substrate.

3. The method of claim 2, wherein steps (a) and (b) are carried out with a voltage applied across the pore.

4. The method of claim 3, wherein the target substrate is a nucleic acid, and wherein said contacting is controlled by a handling enzyme so that the movement of the nucleic acid through the pore and a proportion of the nucleotides in the target sequence interacts with the pore.

5. The method of claim 3, wherein the target substrate is a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant.

6. The method of claim 2, wherein the target substrate is a nucleic acid, and wherein said contacting is controlled by a handling enzyme so that the movement of the nucleic acid through the pore and a proportion of the nucleotides in the target sequence interacts with the pore.

7. The method of claim 2, wherein the target substrate is a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant.

8. An apparatus for sensing a target substrate in a sample, comprising the mutant aerolysin pore of claim 4.

9. The apparatus of claim 8, wherein the target substrate is a nucleic acid sequence, the apparatus further comprising a nucleic acid handling enzyme.

10. A system comprising a membrane having at least one mutant aerolysin pore of claim 4 spanning across the membrane thickness.

11. A construct comprising:

two or more covalently attached monomers derived from a mutant aerolysin monomer;

a homo-oligomeric pore derived from a mutant aerolysin monomer comprising identical mutant monomers; or a hetero-oligomeric pore derived from a mutant aerolysin monomer, wherein at least one of the monomers differs from the others, wherein the mutant aerolysin monomer has a modified aerolysin amino acid sequence comprising one or more amino acid substitutions at one or more of the following positions of SEQ ID NO: 8:

R220, wherein the amino acid substituted into the mutant aerolysin monomer at position R220 is selected from the group consisting of asparagine (N), glutamine (O), leucine (L), lysine (K), tryptophan (W), histidine (H) and alanine (A), R282, wherein the amino acid substituted into the mutant aerolysin monomer at position R282 is selected from the group consisting of asparagine (N), glutamine (O), glutamic acid (E), leucine (L), lysine (K), tryptophan (W), histidine (H) and alanine (A), K238, wherein the amino acid substituted into the mutant aerolysin monomer at position K238 is selected from the group consisting of asparagine (N), arginine (R), leucine (L), tryptophan (W), histidine (H) and alanine (A), K242, wherein the amino acid substituted into the mutant aerolysin monomer at position K242 is selected from the group consisting of asparagine (N), glutamine (O), arginine (R), glutamic acid (E), leucine (L), tryptophan (W), histidine (H) and alanine (A), D216, wherein the amino acid substituted into the mutant aerolysin monomer at position D216 is selected from the group consisting of asparagine (N), serine (S), glutamine (O), arginine (R), glycine (G), tyrosine (Y), glutamic acid (E), leucine (L), lysine (K), cysteine (C) and alanine (A), D222, wherein the amino acid substituted into the mutant aerolysin monomer at position D222 is selected from the group consisting of asparagine (N), serine (S), glutamine (O), arginine (R), glycine (G), tyrosine (Y), glutamic acid (E), leucine (L), lysine (K), cysteine (C) and alanine (A), K244, wherein the amino acid substituted into the mutant aerolysin monomer at position K244 is selected from the group consisting of asparagine (N), serine (S), glutamine (O), arginine (R), glycine (G), tyrosine (Y), aspartic acid (D), glutamic acid (E), leucine (L), cysteine (C) and alanine (A), K246, wherein the amino acid substituted into the mutant aerolysin monomer at position K246 is selected from the group consisting of asparagine (N), serine (S), glutamine (O), arginine (R), glycine (G), tyrosine (Y), aspartic acid (D), glutamic acid (E), leucine (L), cysteine (C) and alanine (A), E252, wherein the amino acid substituted into the mutant aerolysin monomer at position E252 is selected from the group consisting of asparagine (N), serine (S), glutamine (O), arginine (R), glycine (G), tyrosine (Y), aspartic acid (D), leucine (L), lysine (K), cysteine (C) and alanine (A), E254, wherein the amino acid substituted into the mutant aerolysin monomer at position E254 is selected from the group consisting of asparagine (N), serine (S), arginine (R), glycine (G), tyrosine (Y), aspartic acid (D), leucine (L), lysine (K), cysteine (C) and alanine (A), E258, wherein the amino acid substituted into the mutant aerolysin monomer at position E258 is selected from the group consisting of asparagine (N), serine (S), glutamine (O), arginine (R), glycine (G), tyrosine (Y), aspartic acid (D), leucine (L), lysine (K), cysteine (C) and alanine (A), and D209, wherein the amino acid substituted into the mutant aerolysin monomer at position D209 is selected from the group consisting of asparagine (N), serine (S), glutamine (o), glycine (G), tyrosine (Y), glutamic acid (E), leucine (L), lysine (K), cysteine (C) and alanine (A).

12. The construct of claim 11, wherein the mutant aerolysin monomer comprises at least one of the following mutations:
R220A/W/K/Q,
R282A/W,
K238A/N/R/W/H,
K242A/W,
D216A/N/R/Q,
D222A/N/R/Q,
K244A/N/R/Q/D,
K246A/N/R/Q/D,
E252A/N/R/Q,
E254A/N/R,
E258A/N/R/Q,
D209K/A/N/Q/E/C/S/G/Y/L
as well as any combination thereof.

13. The construct of claim 11, wherein the mutant aerolysin monomer comprises at least one of the following mutations:
R220A/W/K/Q,
R282A/W,
K238A/N/R/W,
K242A/W
as well as any combination thereof.

* * * * *